US011092561B2

(12) United States Patent
Gayrard et al.

(10) Patent No.: US 11,092,561 B2
(45) Date of Patent: Aug. 17, 2021

(54) METHOD AND SYSTEM FOR DETERMINING A QUALITY OF HYDROCARBON FLUID

(71) Applicant: MEAS France SAS, Toulouse (FR)

(72) Inventors: Fabien Gayrard, Toulouse (FR); Francois-Xavier Villemin, Toulouse (FR)

(73) Assignee: MEAS FRANCE SAS, Toulouse (FR)

( * ) Notice: Subject to any disclaimer, the term of this patent is extended or adjusted under 35 U.S.C. 154(b) by 248 days.

(21) Appl. No.: 16/405,967

(22) Filed: May 7, 2019

(65) Prior Publication Data

US 2019/0346389 A1 Nov. 14, 2019

(30) Foreign Application Priority Data

May 9, 2018 (EP) .................................... 18290049

(51) Int. Cl.
*G01N 27/06* (2006.01)
*G01N 11/10* (2006.01)
*G01N 33/28* (2006.01)

(52) U.S. Cl.
CPC ............. *G01N 27/06* (2013.01); *G01N 11/10* (2013.01); *G01N 33/2876* (2013.01)

(58) Field of Classification Search
CPC ........ G01N 27/06; G01N 11/10; G01N 33/28; G01N 33/2876; G01N 11/16; G01N 27/08; G01N 11/00; G01N 27/22; G01N 27/221; G01N 27/24; G01N 9/36; G01N 33/2835; G01N 33/2888; G01V 3/26; G01V 3/28
See application file for complete search history.

(56) References Cited

U.S. PATENT DOCUMENTS 7,370,514 B2 5/2008 Halalay et al.
7,581,434 B1 * 9/2009 Discenzo ........... G01N 33/2888 73/53.01
2006/0232267 A1 * 10/2006 Halalay ............. G01N 33/2888 73/53.05
2009/0216471 A1 * 8/2009 Akiyama ........... G01N 33/2876 702/65
2012/0229152 A1 * 9/2012 Katafuchi .......... G01N 33/2876 324/672
2015/0099678 A1 * 4/2015 Abi-Karam .......... C10M 111/06 508/591

* cited by examiner

*Primary Examiner* — Son T Le

(57) ABSTRACT

The invention comprises a method and an analysing system for determining a quality of a hydrocarbon fluid. In an example, the electrical resistivity of the fluid is determined by means of a sensor device. The electrical resistivity is determined over time under predetermined conditions, and a change in the electrical resistivity is monitored over time. A change in fluid visocity may also be determined and monitored over time. The analysing system provides information about an absolute value of a difference of a total base number and a total acid number based on the monitored resistivity change that relates to the quality of the fluid for providing an indication of the remaining useful life of the fluid. In an example, the information about the fluid may correlate to oxidation and/or nitration of the fluid when a change in fluid visocity is below a predetermined threshold.

17 Claims, 13 Drawing Sheets

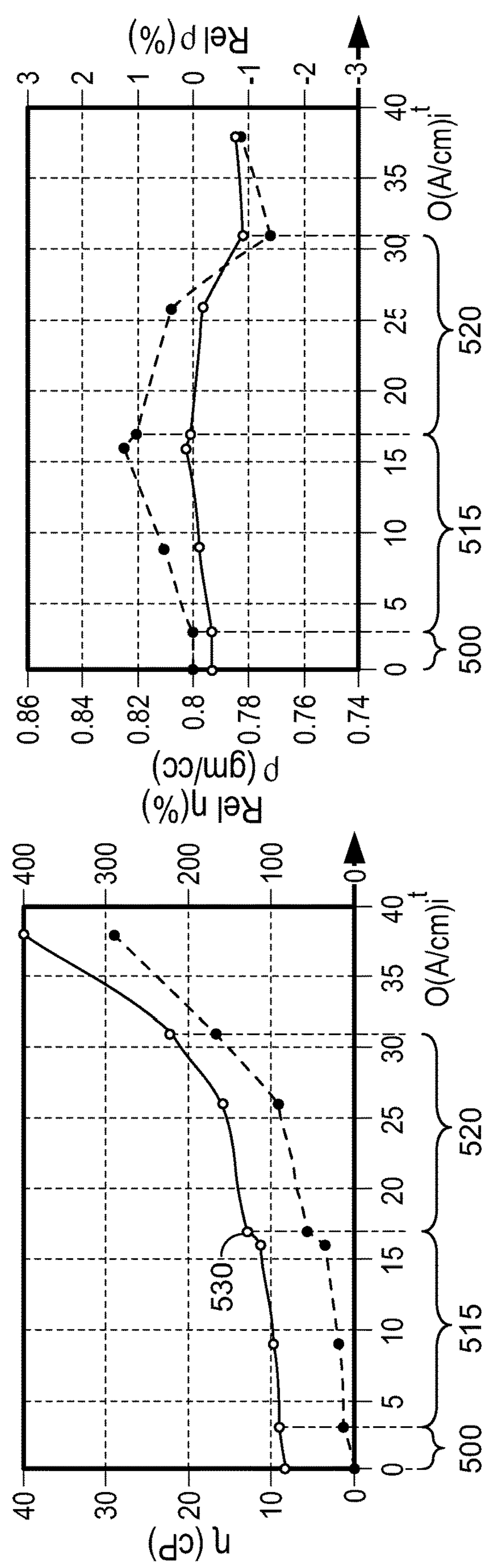
Fig. 7
Fig. 9
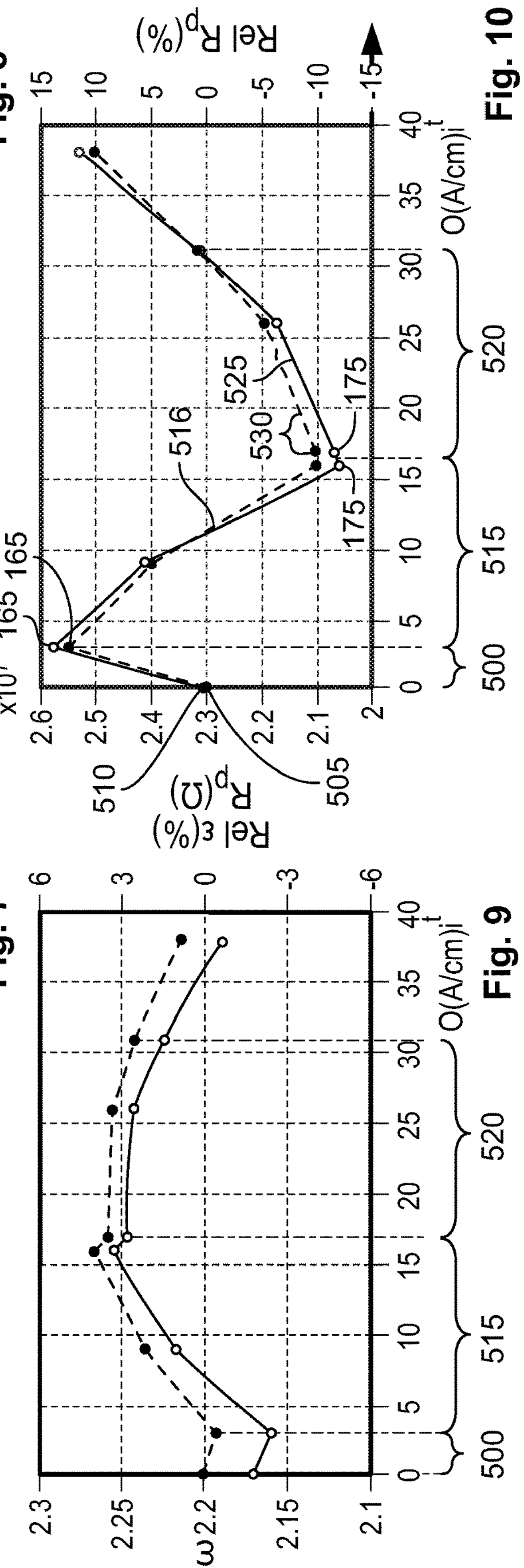
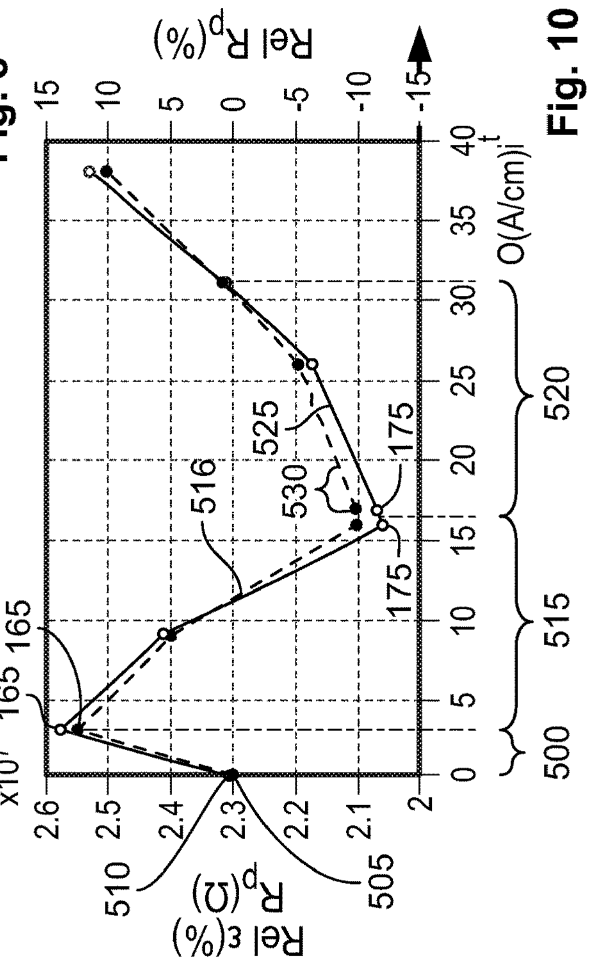
Fig. 8
Fig. 10

METHOD AND SYSTEM FOR DETERMINING A QUALITY OF HYDROCARBON FLUID

RELATIONSHIP TO COPENDING PATENT APPLICATION

This patent application claims priority to European Patent Application No. 18290049.8 filed on May 9, 2018, which application is hereby incorporated by reference in its entirety.

FIELD

A method for determining a quality of an oil and an analysing system for determining the quality of the hydrocarbon fluid with an information about a total base number, a total acid number, oxidation and/or nitration is disclosed herein.

BACKGROUND

U.S. Pat. No. 7,370,514 B2 teaches a method for determining the remaining useful life of a quantity of oil in use in fluid lubrication of an operating mechanism, wherein the method comprises the following steps: repeatedly determining resistivity (ρ) values of the oil at a predetermined oil temperature during operating time intervals of the mechanism; recording a resistivity-time ρ(t) history of the oil such that, as successive resistivity values starting with an initial value are accumulated with elapsed operating time, a continuous ρ(t) linear curve is formulated that includes: a first portion with a slope of dρ/dt>0 up to a first time t1 during which values of ρ increase and maxima at t1 where dρ/dt=0 with a corresponding $\rho_{max}$, comparing, from time to time, the then existing portion of the ρ(t) curve with similar predetermined data on a similar or functionally comparable oil composition; using the comparison to predict the remaining useful life of the oil; continuing to record a resistivity-time ρ(t) history of the oil so that a continuous ρ(t) linear curve is formulated that further includes: a second portion with a slope of dρ/dt<0 during which values of ρ decrease up to a second time t2, minima at t2 where dρ/dt=0 with a corresponding $\rho_{min}$, and a third portion where dρ/dt>0; continuing to compare, from time to time, the then existing portions of the ρ(t) curve with similar predetermined data on a similar or functionally comparable oil composition and using the comparison to predict the remaining useful life of the oil; continuing to record a resistivity-time ρ t) history of the oil in the third portion of the ρ(t) curve until time t3 when there is a sudden increase in the value of the time derivative of the resistivity indicating that the useful life of the oil has been depleted; and then generating a signal indicating that the useful life of the oil has been depleted.

SUMMARY

It is the object of the present invention to provide a method and a system for precisely determining a quality of a hydrocarbon fluid.

The object of the invention is achieved by a method and an analysing system, wherein the method for determining a quality of an hydrocarbon fluid comprises the following steps: determining an electrical resistivity of the hydrocarbon fluid by means of a sensor device, repeating the determining step for the electrical resistivity over time, monitoring the resistivity of the hydrocarbon fluid over time, determining a use of the hydrocarbon fluid under predetermined conditions, determining a change of resistivity over time, monitoring the change of resistivity of the hydrocarbon fluid over time, providing a quality information about an absolute value of a difference of a total base number and a total acid number on the basis of the monitored change of resistivity.

The method is particularly simple and cost-effective. Furthermore, by this method and the analysing system an information about the quality of the hydrocarbon fluid regarding a difference of the total base number and the total acid number can be provided during the use of the hydrocarbon fluid in a machine without a cost-intensive and time-consuming physical and chemical analysis of the hydrocarbon fluid.

In a further embodiment a predetermined decrease of the electrical resistivity over time is determined. Furthermore, a predetermined increase of the electrical resistivity over time following the decrease of the electrical resistivity over time is determined, wherein, when determining the increase of the electrical resistivity following the decrease, an information about an end of a useful lifetime of the hydrocarbon fluid regarding the absolute value of the difference of the total base number and the total acid number is provided.

In a further embodiment, the following steps are performed: determining a first time period by detecting a further predetermined increase of the electrical resistivity over time, determining a second time period following the first time period by detecting the predetermined decrease of the electrical resistivity over time, determining a beginning of a third time period following the second time period by detecting the predetermined increase of the electrical resistivity over time.

In a further embodiment a dynamic viscosity of the hydrocarbon fluid by means of the sensor device is determined, wherein the determining step for the viscosity over time is repeated, wherein a change of viscosity of the hydrocarbon fluid over time is determined, wherein a predetermined increase of the change of viscosity is determined, wherein the increase of the change of viscosity in combination with the increase of electrical resistivity is determined and an information about the quality of the hydrocarbon fluid regarding oxidation and/or nitration of the hydrocarbon fluid and the difference of the total base number and the total acid number is provided. Therefore, conclusions can be made, for example about an aging of the hydrocarbon fluid or a mechanical wear of the machine.

In a further embodiment, the change of the viscosity is compared to a predetermined threshold, wherein the information about the quality of the hydrocarbon fluid correlates to oxidation and/or nitration of the hydrocarbon fluid and the difference of the total base number and the total acid number when the change of viscosity exceeds the predetermined threshold, wherein the information about the quality of the hydrocarbon fluid correlates with the difference of the total base number and the total acid number of the hydrocarbon fluid when the change of viscosity is below the predetermined threshold.

In a further embodiment, wherein the information on the quality of the hydrocarbon fluid regarding oxidation and/or nitration of the hydrocarbon fluid and the difference of the total base number and the total acid number is provided when the predetermined increase the change of viscosity exceeding the predetermined threshold, are detected in a first predetermined time period, preferably are determined simultaneously, wherein the first predetermined time period is shorter than the first determined time period and/or the second determined time period.

In a further embodiment, depending on the information an information signal is provided to signalize that the hydrocarbon fluid is about to reach its end of useful life and a change of the hydrocarbon fluid has to be carried out.

In a further embodiment, after determining the increase of the electrical resistivity, the determining step(s) of determining the electrical resistivity is/are stopped. Alternatively, after providing the information the electrical resistivity is only determined for a second predetermined time period, wherein the second predetermined time period is shorter than a backup time in which the hydrocarbon fluid still can be used before the hydrocarbon fluid is completely degraded.

In a further embodiment, the information is stored in a memory, preferably in an error register, wherein the information is taken into account for an error analysis for a mechanical machine or a system, which uses the hydrocarbon fluid.

In a further embodiment, the method comprises the following steps: applying a variable frequency input signal to a measurement circuit coupled with the mechanical resonator, varying the frequency of the frequency input signal over a predetermined frequency range to obtain a frequency-dependent response signal of the mechanical resonator, determining the electrical resistivity of the hydrocarbon fluid on the basis of the mechanical resonator response, repeating the applying, varying and determining steps over time.

In a further embodiment, the viscosity of the hydrocarbon fluid is determined on the basis of the response signal, wherein the viscosity and the electrical resistivity are determined on the basis of the same response signal.

In a further embodiment, an information about a start value of the total acid number and/or a start value of the total base number of the hydrocarbon fluid at the beginning of the use of the hydrocarbon fluid is provided, wherein on the basis of a predetermined parameter the resistivity and the start value of the total acid number and/or start value of the total base number an actual value of the difference of the total acid number and the total base number is determined, wherein the actual absolute value of the difference of the total acid number and the total bases number is provided.

In a further embodiment, an information about a start value of the total acid number and/or a start value of the total base number of the hydrocarbon fluid is provided at the beginning of the use of the hydrocarbon fluid, wherein on the basis of a predetermined parameter the resistivity and the start value of the total acid number and/or start value of the total base number an actual value of the of the difference of the total acid number and the total base number is determined, wherein the actual absolute value of the difference of the total acid number and the total base number is provided.

In a further embodiment, a predetermined end value of the absolute value of the difference of the total acid number and the total base number of the hydrocarbon fluid corresponding to an end of the life of the hydrocarbon fluid is provided. Alternatively, or additionally a predetermined end value of electrical resistivity of the hydrocarbon fluid corresponding to an end of the life of the hydrocarbon fluid is provided. On basis of a further predetermined parameter, the predetermined start value, the predetermined end value and/or of the absolute value of the difference of the total acid number and the total base number) and the determined actual electrical resistivity a remaining lifetime of the hydrocarbon fluid regarding the absolute value of the difference of the total acid number and the total base number is determined. An information of the remaining useful lifetime of the hydrocarbon fluid is provided.

BRIEF DESCRIPTION OF THE DRAWINGS

In the following, the embodiments of the invention will be explained in more detail in conjunction with the accompanying drawings, in which:

FIG. 7 depicts a diagram of the dynamic viscosity $\eta$ and the relative viscosity evolution $Rel\eta(t)$ over an oxidation O and time t at a predetermined temperature $T_1$;

FIG. 8 shows a diagram of a density $\rho$ and a relative viscosity evolution $Rel\rho$ over the oxidation O and time t at the predetermined temperature $T_1$;

FIG. 9 shows a diagram of the dielectric constant $\varepsilon$ and a relative dielectric constant evolution $Rel\varepsilon$ over the oxidation O and time t at the predetermined temperature $T_1$;

FIG. 10 shows a diagram of an electrical resistance $R_p$ (t) and a relative electrical resistance evolution $RelR_p$ (t) over the oxidation O and time t at the predetermined temperature $T_1$;

DESCRIPTION

Figure 1:
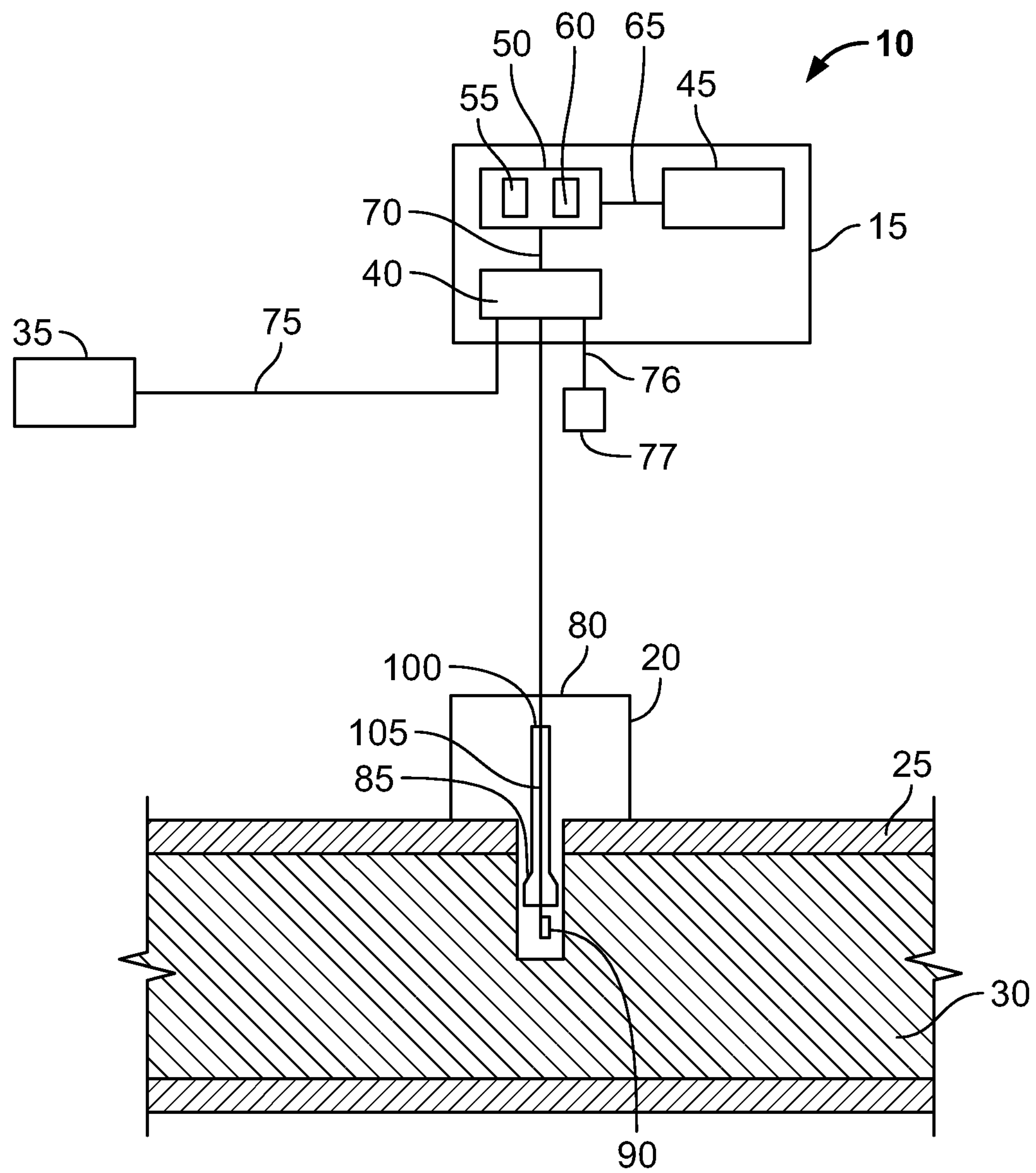
FIG. 1 shows a schematic representation of a system.

FIG. 1 shows a schematic representation of a system 10. The analysis system 10 comprises a control unit 15, a sensor device 20 and a signalling device 35. Furthermore means 25 for containing a hydrocarbon fluid 30 are provided.

The control unit 15 comprises an interface 40, a data storage 45 and a measurement circuit 50. The measurement circuit 50 comprises a signal generator 55 and a receiver 60. The measurement circuit 50 is connected to the data storage 45 by a first connection 65. The interface 40 is connected to the measurement circuit 50 by means of a second connection 70. The signalling device 35 is connected to the interface 40 by a third connection 75. Also, the interface 40 can be connected to an error storage 77 by means of a further connection 76.

The sensor device 20 comprises a compartment 80, a mechanical resonator 85 and for example a sensor 90. The sensor 90 can be a temperature sensor. The sensor 90 and the mechanical resonator 85 are both arranged in the compartment 80. The mechanical resonator 85 is preferably a tuning fork resonator. The mechanical resonator 85 can also be an array of tuning fork resonators, wherein each tuning fork resonator comprises a separate different resonant frequency.

The mechanical resonator 85 is connected to the interface 40 by means of a fourth connection 100. The sensor 90 is connected to the interface 40 by means of a fifth connection 105. The means 25 for containing the hydrocarbon fluid 30 can be for example a tube, a container or for example a fluid tank. The means 25 for containing the hydrocarbon fluid 30 can also be a fluid reservoir, a process line, a pressurized high flow conduit (e.g. engine or gallery), for example on and off highway vehicles, a heating, ventilation and air conditioning system, a compressor, an industrial equipment, an internal combustion engine, a gear box and/or a turbine.

The hydrocarbon fluid 30 is for example a motor oil of a combustion engine, particularly an additive conductive oil. The additive can reduce an electrical resistivity of the hydrocarbon fluid 30. The hydrocarbon fluid 30 can also be a hydraulic fluid for a hydraulic circuit, for example for a construction machine or a construction vehicle.

The mechanical resonator 85 and the sensor 90 are arranged in the hydrocarbon fluid 30. The sensor 90 measures a temperature of the hydrocarbon fluid 30 and provides a temperature signal corresponding to the measured temperature T of the hydrocarbon fluid 30. The temperature signal is transmitted to the interface 40 via the fifth connection 105. The interface 40 provides the measurement circuit 50 with the temperature signal by means of the second connection 70.

Over the lifetime of the hydrocarbon fluid 30, the quality of the hydrocarbon fluid changes through several internal and external influences. Depending on the influences, physical and/or chemical parameters (for example a (electrical) resistivity P, a dielectric constant ε, a density ρ, a dynamic viscosity η) change over time.

The signalling device 35 can comprise a display, a sounder, a lamp and/or a strobe.

Figure 2:
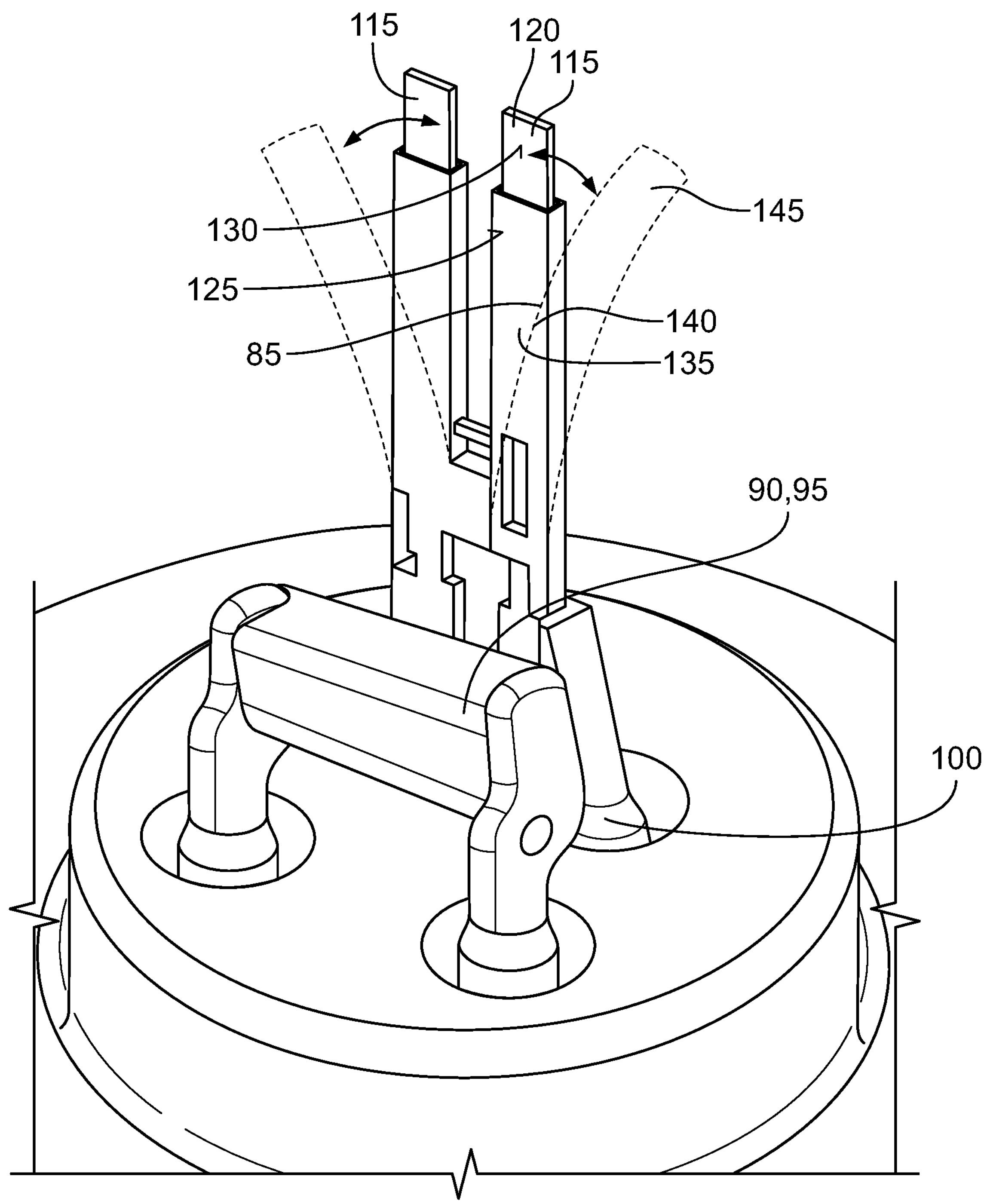
FIG. 2 depicts a perspective view on a sensor device of the system.

FIG. 2 shows a perspective view of the sensor device 20. The mechanical resonator 85 is for example a tuning fork resonator and comprises two tines 115. Each tine 115 comprises preferably a quartz crystal centre section 120 and at least one electrode 125 connected to the quartz crystal centre section 120. The electrode 125 is electrically connected to the fourth connection 100. Preferably the electrode 125 is arranged on a shell surface 130 of the quartz crystal centre section 120. Preferably the electrode 125 comprises a first electrode section 135 and at least a second electrode section 140, wherein the first electrode section 135 is arranged on one side of the shell surface 130 and the other electrode section 140 is arranged on another side, preferably an opposite side of the shell surface 130.

When the signal generator 55 provides the frequency signal to the electrode 125, the electrode 125 provides an electric field 145 which is not concentrated between the electrode sections 135, 140 but instead interacts with the surrounding hydrocarbon fluid 30 outside of the tine 115 and the two tines 115 oscillate in the hydrocarbon fluid 30.

The frequency signal can comprise a sinusoidal excitation voltage, which is provided to the electrodes 125. The frequency signal causes the electric field 145 between the electrodes 125 arranged at the two tines 115. The electric field 145 causes a force on the tines 115 so that the tines 115 vibrate with the frequency of the frequency signal. The kind of vibration of the tines 115 depends on the fluid properties of the hydrocarbon fluid 30.

As a response signal, the vibration induces a current in the electrodes 125. A ratio of the excitation voltage of the frequency signal to the induced current of the response signal allows a measuring of the impedance of the mechanical resonator 85 which shows a dependence of the frequency signal, the elastic properties of the mechanical resonator 85 and the properties of the hydrocarbon fluid 30. For example, the mechanical resonator 85 has a sharp resonance frequency at about 31 kHz. In the hydrocarbon fluid 30 the resonance frequency and/or an amplitude of the response signal are different due to the mass load of the hydrocarbon fluid 30 and fractional forces of the hydrocarbon fluid 30 on the mechanical resonator 85.

The response signal is transmitted to the interface 70 via the fourth connection 105. The interface 70 provides the response signal to the receiver 60.

Figure 3:
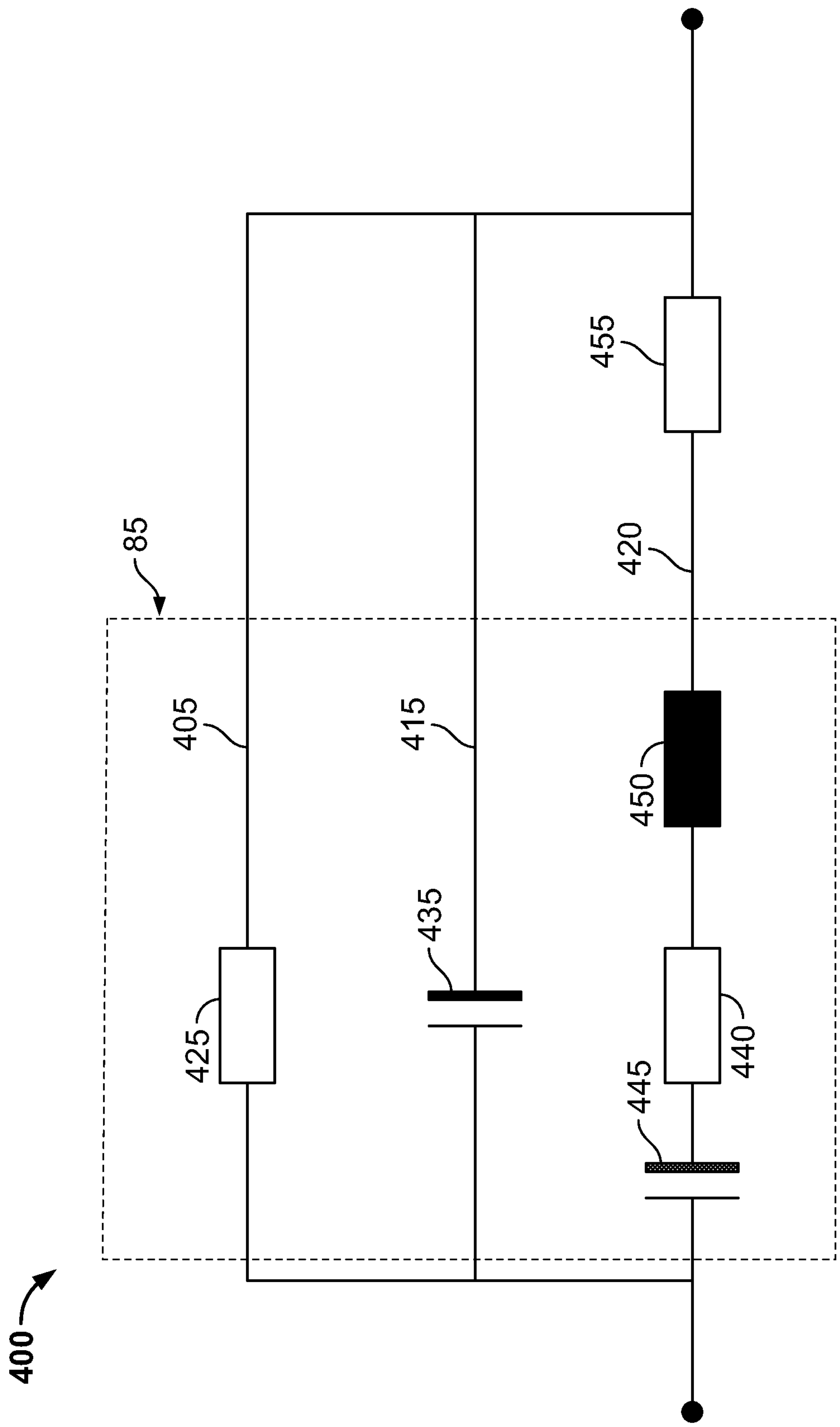
FIG. 3 shows a mechanical resonator equivalent to an electrical model.

FIG. 3 shows an electrical equivalent model 400 of the mechanical resonator 85. The electric model 400 comprises three electrical paths 405, 415, 420 switched in parallel to one another. In the first electrical path 405, the electrical model 400 comprises the electrical resistance 425 ($R_p$). In the second electrical path 415, the electrical model 400 comprises a capacitance 435 ($C_p$). In the third electrical path 420 the electrical model 400 comprises a further resistance 440 ($R_0$), a second capacitance 445 ($C_s$), and an inductance 450 ($L_0$). Additionally, the electrical model 400 comprises an additional term 455 which is arranged in the third path 420. The additional term 455 depends on hydrocarbon fluid properties. The further resistance 440 ($R_0$), the second capacitance 445 ($C_s$), the inductance 450 ($L_0$) and the additional term 450 are arranged serially.

A complex impedance Z in air of the mechanical resonator 85 is modelled by the following formula:

$$Z_{TF}(\omega)=R_P \| C_{P,0} \| (R_0+i\omega L_0+1/(i\omega C_s)) \quad (1)$$

The serial second capacitance $C_s$, the further resistance $R_0$ and the inductance $L_0$ only depend on geometrical parameters of the mechanical resonator 85.

The impact of the hydrocarbon fluid 30 is described by the additional term 455 by means of the following formula:

$$Z(\omega)=Ai\omega\rho+B\sqrt{\omega\rho\eta}(1+i) \quad (2)$$

wherein ω is the frequency of the frequency signal, η is the dynamic viscosity of the fluid in which the mechanical resonator 85 is arranged, ρ is the density of the fluid in which the mechanical resonator 85 is arranged and A and B are constants depending on the mechanical resonator geometry.

The dielectric constant ε and/or the relative permittivity of the hydrocarbon fluid 30 and an electrical resistivity P are measured due to the parallel capacitance $C_p$ and the parallel resistance $R_p$. In air $C_{p,0}$ and $C_{P,\ air}$ are identical because ε(air)=1.

$$C_p(\varepsilon) = (\varepsilon - 1)\frac{dCp}{d\varepsilon} + C_{p,0} \quad (3)$$

$$R_p = f_{t1}(P),\ P = f_{t2}(\eta) \quad (4)$$

The electrical resistivity P can be considered as a drag force encountered by free charge carriers of the hydrocarbon fluid 30 moving through the hydrocarbon fluid 30 under the application of the electrical field 145. The electrical resistivity P depends on the viscosity η, on a density of the free charge carriers and on specific hydrocarbon fluid 30 chemicals.

The electrical resistance $R_p$ is a function of the electrical resistivity P. The electrical resistance $R_P$ represents a measure for the electrical resistivity P. The electrical resistance $R_P$ and the electrical resistivity P can be easy converted into each other.

In a first approximation the parallel resistance $R_P$ can be modelled in a simple linear form:

$$R_P=H+I\cdot T \tag{5}$$

wherein T is the actual temperature of the hydrocarbon fluid 30 in degrees Kelvin and H and I are hydrocarbon fluid dependent constants.

The hydrocarbon fluid 30 can be composed of paraffinic, naphthenic and aromatic hydrocarbons, for example mixed with at least the additive compounds, preferably mixed with different additives to fulfil several functions, for example lubrication, sealing, power transmission, engine part cooling, cleaning and/or acid component neutralisation.

During its lifetime, the hydrocarbon fluid 30 degenerates. The components of the hydrocarbon fluid 30 change through several impacts, e.g. friction, heat, incorrect ceiling and/or adding different substances to the hydrocarbon fluid 30. For example, adding polar components or charge carriers degeneration products can be created during aging of the hydrocarbon fluid 30. In parallel, base additives are depleted which decreases protection against acidification.

An electrical and chemical behaviour of the hydrocarbon fluid 30 have a direct impact on the dielectric constant ε and the parallel resistance $R_p$.

The dielectric constant ε or relative permittivity is a ratio of hydrocarbon fluid permittivity on vacuum permittivity ($C_{P,\,0}$). The dielectric constant ε represents the capacity of the hydrocarbon fluid 30 to be polarized under the application of the electric field 145 of the electrode 125. The polarization is the consequence of the reorientation of molecular dipoles in the hydrocarbon fluid 30. During hydrocarbon fluid 30 aging, dipole moments could change because of microscopic chemical reactions like oxidation or nitration of the hydrocarbon fluid 30 or because of the addition of polar contaminants such as water or soot.

The hydrocarbon fluid 30 also provides an alkaline reserve to prevent acidification. The alkaline reserve can be measured due to the total base number (TBN) value. In the same way, acidity can be measured by the total acid number (TAN). The total acid number (TAN) and the total base number (TBN) comprise the measurement unit mgKOH/g, which corresponds to the equivalent mass of potassium hydroxide required to neutralize one gram of solution.

The dielectric constant ε has the following equation:

$$\varepsilon=F+GT \tag{6}$$

wherein T is the temperature of the hydrocarbon fluid 30 in degrees Kelvin, F and G are hydrocarbon fluid 30 dependant constants.

Figure 4:
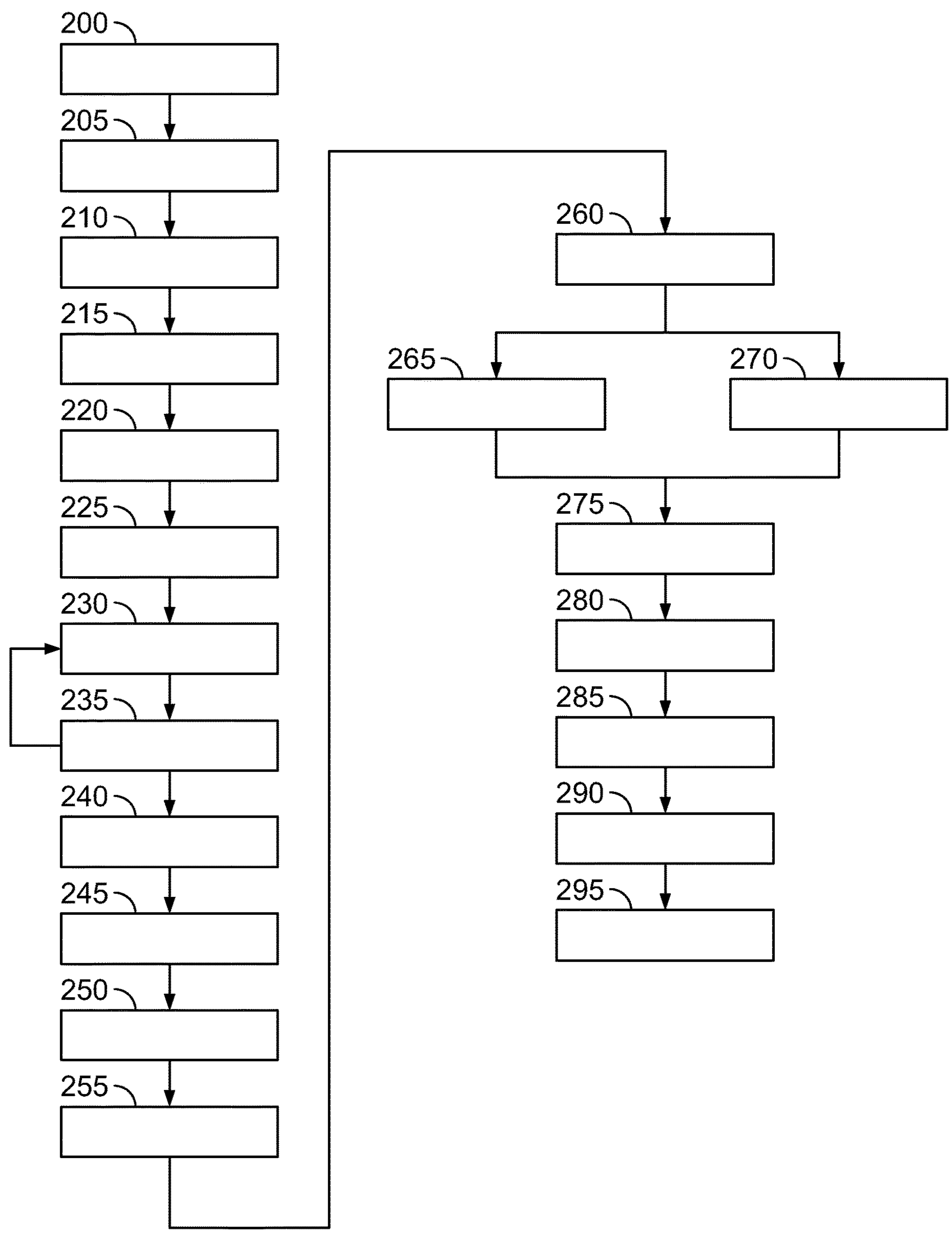
FIG. 4 shows a flow chart of a method according a first embodiment for determining the quality of a hydrocarbon fluid of the system.
Figure 5A:
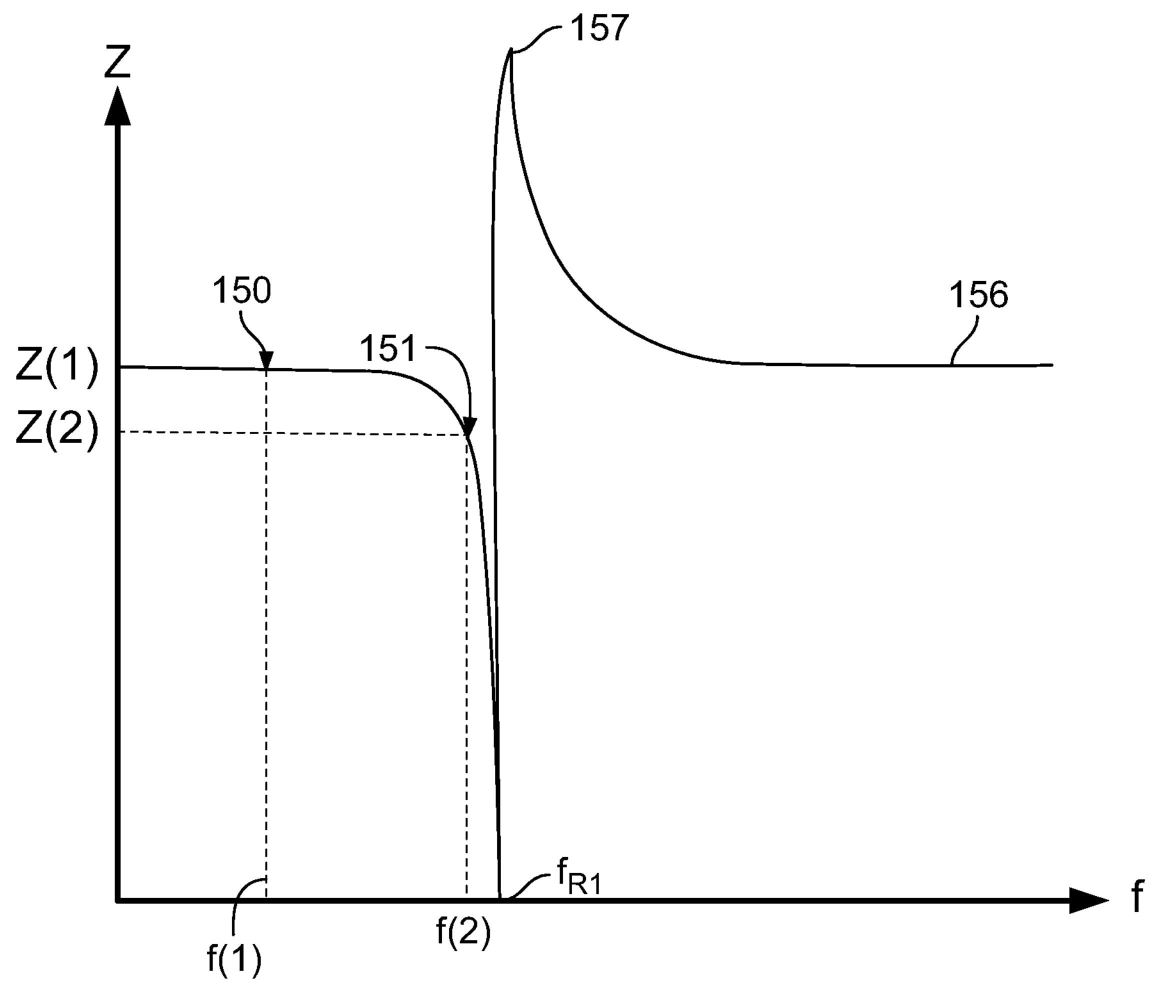
FIG. 5*a* shows a diagram of the impedance Z over the frequency f of calibration response signals.

FIG. 4 shows a flow chart of a method according to a first embodiment. FIG. 5*a* shows a diagram of the impedance Z over the frequency f of calibration response signals.

The first four steps 200-215 are performed to calibrate the measurement system 10.

In the first step 200, the mechanical resonator 85 is arranged in a predetermined material—for example a vacuum or air.

In a second step 205, the signal generator 55 is activated and in a first time step provides a first frequency signal with a first frequency f(1). The first frequency f(1) could for example be 21 kHz. The first frequency could also be a different frequency, for example 25.5 kHz.

The first frequency signal is transmitted via the second and fourth connection 70, 100 and the interface 40 to the mechanical resonator 85. The first frequency signal stimulates the mechanical resonator 85 to vibrate with the first frequency f(1). The predetermined material influences the vibration of the mechanical resonator 85, for example by damping the mechanical resonator 85. The mechanical resonator 85 provides a first calibration response signal 150 corresponding to the predetermined material. The first calibration response signal 150 has a first value Z(1) for the impedance Z at the first frequency f(1).

The first calibration response signal 150 is transmitted from the mechanical resonator 85 to the receiver 60 via the second and fourth connection 70, 100 and the interface 40. The measurement circuit 50 saves the first calibration response signal 150 related to an information to the first frequency signal for the first time step in the data storage 45.

In a third step 205, the signal generator 55 provides in a second time step a second frequency signal with a second frequency f(2), wherein the second frequency f(2) is different from the first frequency f(1). For example, the second frequency f(2) is increased or decreased to the first frequency f(1) in a 60 hertz step. Of course, the second frequency f(2) can also be different. The first and second time step take up less than a few seconds.

In the second time step, the second frequency signal is provided to the mechanical resonator 85 and the mechanical resonator 85 provides a second calibration response signal 151 with a second value Z(2) for the impedance Z to the measurement circuit 50. The measurement circuit 50 saves the second calibration response signal 151 related to an information to the second frequency signal for the second time step in the data storage 45.

To calibrate the system 10, the signal generator 55 repeats the second step 205 and the third step 210 and changes the frequency f over the time steps over the predetermined frequency range. The calibration response signals 150, 151 comprise a first distribution 156 of the impedance Z over frequency f. The first distribution 156 comprises a first resonance peek 157 at a first resonance frequency $f_{R1}$.

Additionally, in the second and third step 205, 210 the calibration response signals 150, 151 can be filtered to avoid any false detection of the fluid properties.

In a fourth step 215, the measurement circuit 50 calculates the parallel resistance $R_p$ and a dynamic viscosity η for the predetermined material on the basis of a predetermined parameter saved in the data storage 45 and the first distribution 156. The predetermined parameter can be an algorithm and/or a characteristic diagram and/or a table. The system 10 is calibrated by adjusting the predetermined parameter by comparing the determined resistance $R_P$ and the dynamic viscosity η in comparison to a known and predetermined electrical specific resistance $R_P$ and the dynamic viscosity η for the predetermined material. The adopted predetermined parameter is saved in the data storage 45.

Figure 5B:
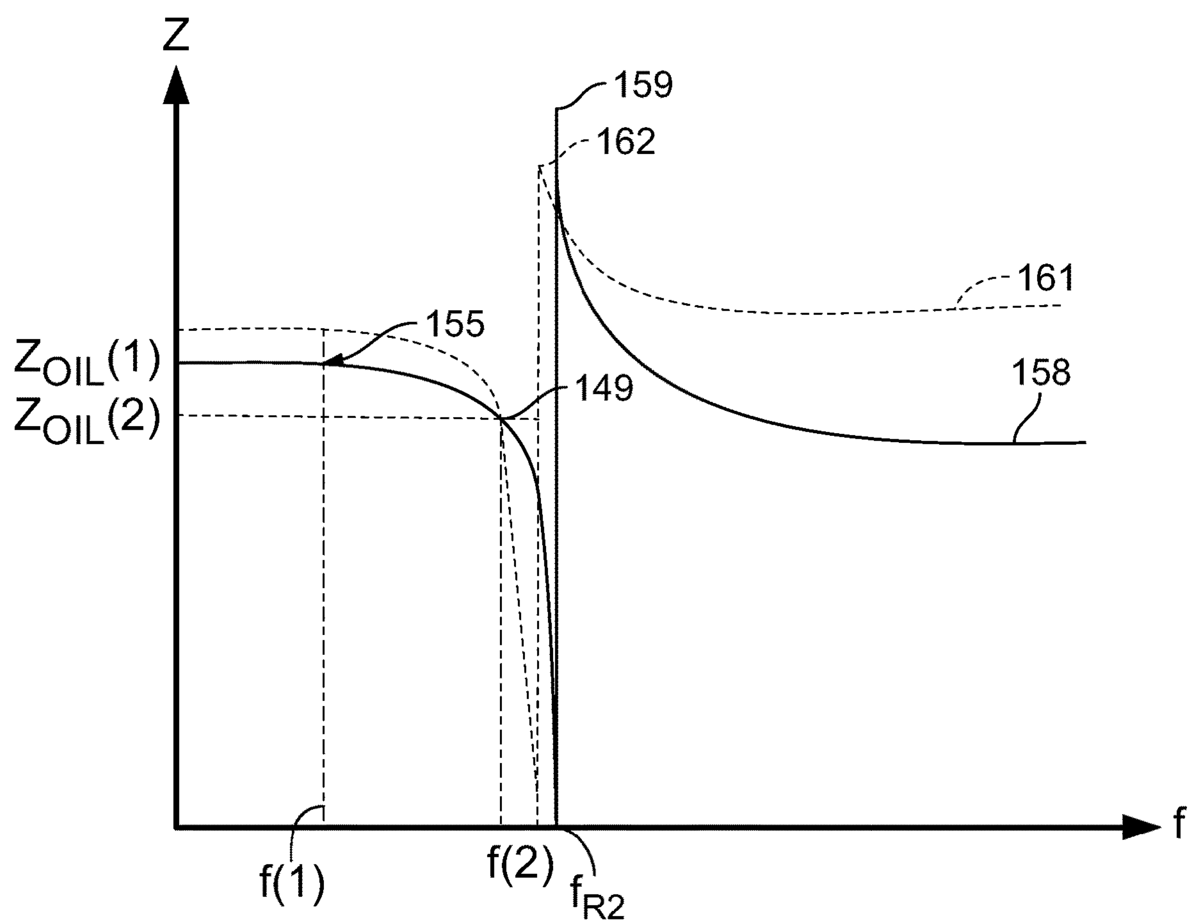
FIG. 5*b* shows a diagram of the impedance Z over the frequency f of different response signals.

FIG. 5*b* shows a diagram of the impedance Z over the frequency f of different response signals.

After calibration of the system 10, the system 10 is arranged in a fifth step 220, for example in a vehicle with the mechanical resonator 85 being surrounded by the hydrocarbon fluid 30. In the first embodiment, the exact composition of the hydrocarbon fluid 30 is unknown.

In a sixth step 225 the hydrocarbon fluid 30 is changed in case the provided hydrocarbon fluid 30 was already used for a predetermined first time period, e.g. for more than 5 hours. In case the hydrocarbon fluid 30 is new or has been used for less than the predetermined first time period, the sixth step 225 is skipped. An information on the occurrence of the change of the hydrocarbon fluid 30 can be bought by the user or can be detected by an additional specific function and/or a further sensor.

The seventh and eight step 230, 235 are basically identical to the second and third steps 205, 210.

In the seventh step 230, in a first time step of the measurement of the hydrocarbon fluid 30 the signal generator 55 provides the first frequency signal with the first frequency f(1) to the mechanical resonator 85. The mechanical resonator 85 provides a first measurement response signal 155 corresponding to the hydrocarbon fluid 30. The first measurement response signal 155 has a first impedance value $Z_{Oil}(1)$ at the first frequency f(1).

The first measurement response signal 155 of the mechanical resonator 85 is provided from the mechanical resonator 85 to the receiver 60.

The measurement circuit 50 saves the first measurement response signal 155 in the data storage 45 related to an information on the first frequency signal, especially an information on a measurement time t when the first frequency signal is provided.

In the eight step 235, the signal generator 55 changes the frequency f of the frequency input signal in a second time step to the second frequency f(2) and the mechanical resonator 85 obtains a frequency-dependent second measurement response signal 149 for the receiver 60. The second measurement response signal 149 has a second value $Z_{Oil}(2)$ for the impedance Z at the second frequency f(2).

The measurement circuit 50 saves the second measurement response signal 149 in the data storage 45 related to an additional information, particularly an information on the measurement time t when the second frequency signal is provided.

The signal generator 55 repeats the seventh and eight step 230, 235 and changes the frequency f over the time steps over the predetermined frequency range and the receiver 60 obtains the frequency-dependent measurement response signals 155, 149 of the mechanical resonator 85 and the measurement response signals 156, 149 are stored in the data storage 45.

The measurement response signals 156, 49 comprise a second distribution 158 of the impedance Z over frequency f. The second distribution 158 comprises a second peek 159 at a second resonance frequency $f_R$. The second distribution 158 depends on the composition of the hydrocarbon fluid 30 and has a different characteristic compared to the first distribution 156 (cf. FIG. 5*a*).

In a ninth step 240 which can be performed parallel or serial to the seventh and/or eight step 230, 235, the sensor 90 measures the temperature T of the hydrocarbon fluid 30 and provides a temperature signal to the measurement circuit 50. The measurement circuit 50 saves the temperature T with an information on a time, preferably the measurement time t when the first frequency signal was provided, in the data storage 45.

In a tenth step 245, the measurement response signal(s) 155, 149 can be filtered in at least one filtering step 300 to 335.

Figure 6:
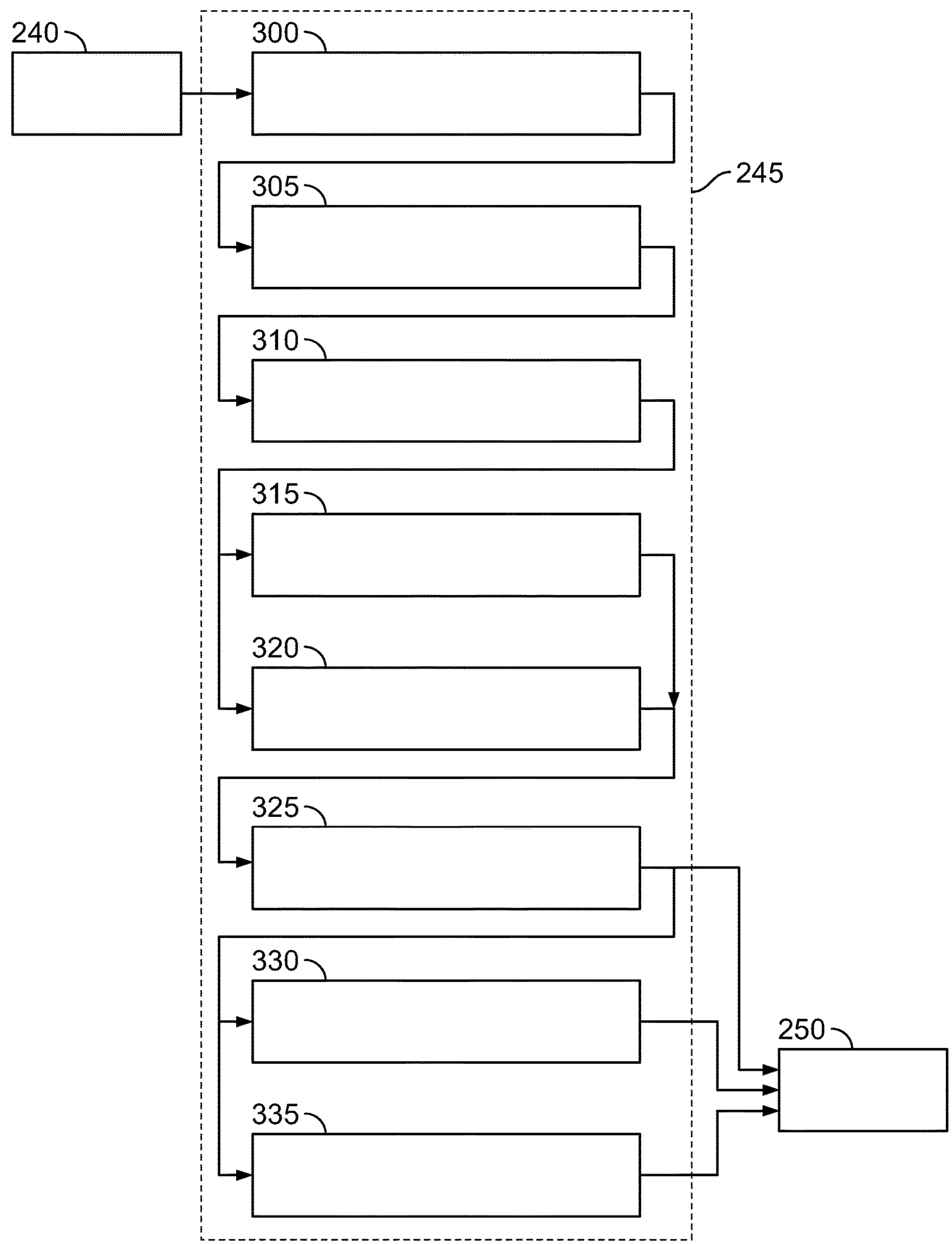
FIG. 6 shows a flow chart for filtering a measurement response signal.

FIG. 6 shows a filtering method for filtering the measurement response signal 155, 149.

In a first filtering step 300, the measurement circuit 50 compares the measurement response signal 155 with a predetermined filter parameter. Whenever the measurement circuit 50 detects that the measurement response signals 155, 149 of the mechanical resonator 85 relate to a hydrocarbon fluid 30 for which the system 10 is not specified, the measurement circuit 50 ignores said measurement response signal 155, 149.

The first filtering step 300 can also be performed by the sensor device 20 wherein the sensor device 20 only provides the measurement response signal 155, 149 when the measurements response signal 155, 149 relates to a hydrocarbon fluid 30 for which the system 10 is specified.

In a second filtering step 305, the measurement circuit 50 can filter the measurement response signals 155, 149, which are allocated to an information that signalizes that the response signal 155, 149 is determined under predetermined conditions. For example, the measurement circuit 50 can delete or ignore all response signals in the further steps that are allocated to the temperature information that the temperature is over a predetermined temperature threshold, for example 100° C. in order to e.g. avoid an evaporation process of water in the hydrocarbon fluid 30.

In a third filtering step 310, the measurement circuit 50 carries out a noise filtering for the saved measurement response signals 155, 149 and deletes all measurement response signals 155, 149 which comprise a noise signal above a predetermined level.

For example, a simple infinite input response filter can be implemented in the measurement circuit 50. A filter order could also be adapted depending on specific system requirements (e.g. temperature gradient) for the system 10. The third filtering step 310 can be different from other filtering steps.

In a fourth filtering step 315, the measurement circuit 50 can determine an actual temperature model on the basis of a predetermined temperature model for the hydrocarbon fluid 30 and at least two measurements of the temperature T of the hydrocarbon fluid 30 and at least two measurement response signals 155, 149. For this purpose, the formulas (4) to (6) can be utilized.

It is particularly advantageous if the fourth filtering step 315 is only performed after a change of the hydrocarbon fluid 30 or in a second predetermined period of time after the hydrocarbon fluid change.

When the measuring circuit 50 detects that the hydrocarbon fluid 30 is not changed, the measurement circuit 50 performs a fifth filtering step 320 instead of the fourth filtering step 315.

In the fifth filtering step 320, the measurement circuit 50 can determine a dynamic temperature model on the basis of a predetermined temperature model saved in the data storage 45. The measurement circuit 50 can update the dynamic temperature model on the basis of the measured temperature T.

The dynamic temperature model can use further information on the hydrocarbon fluid 30 determined from the measurement response signal 155 saved in the data storage.

In a sixth filtering step 325, the measurement circuit 50 temperature compensates the measurement response signals 155, 149 in a second predetermined time period after the hydrocarbon fluid change on the basis of an actual temperature model and the measured temperature T to temperature compensated measurement response signals at a predetermined temperature $T_1$.

The measurement circuit 50 temperature compensates all measurement response signals 155, 149 after the second predetermined time period after the hydrocarbon fluid change on the basis of the dynamic temperature model and the measured temperature T of the hydrocarbon fluid 30 to a temperature compensated measurement response signals at the predetermined temperature $T_1$. The predetermined temperature $T_1$ can for example be 120° C. The temperature-compensated measurement response signals are saved in the data storage 45. Due to the temperature-compensated measurement response signals in the data storage 45, different measurements of the hydrocarbon fluid 30 taken at different temperatures T are comparable and thus can provide better analyses of the temperature-compensated measurement response signals. The temperature measurement response signals comprise a third distribution 161 (dashed line in FIG. 5*b*) of the impedance Z over frequency f. The third distribution 161 comprises a third pic 162 (cf. FIG. 5*b*).

In a seventh filtering step 330, the measurement circuit 50 calculates values of the dynamic viscosity η and at least of the electrical resistance $R_P$ for each measurement time t on the basis of the same saved temperature compensated measurement response signals at the measurement time t, particularly the third distribution 161 and the third peek 162 in relation to the calibration response signals 150, 151 and on the basis of the predetermined adopted parameter at the predetermined temperature $T_1$ for each measurement time t. By means of the calculation, an indirect measurement of the dynamic viscosity η(t) and the electrical resistance $R_p(t)$ can be provided.

Furthermore, the measurement circuit 50 can calculate values of the dielectric constant ε and/or values of the density ρ on the basis of the saved temperature-compensated measurement response signals, particularly the third distributions 161 and the third peek 162 in relation to the calibration response signals 150 and on the basis of the second predetermined parameter at the predetermined temperature $T_1$.

The measurement circuit 50 saves the calculated values together with the corresponding measurement time t information in the data storage 45.

Additionally, the measurement circuit 50 calculates an absolute dynamic viscosity evolution Absη(t) between the dynamic viscosity η(t) and a dynamic viscosity $\eta_i$ when the hydrocarbon fluid 30 has just been changed at the predetermined temperature $T_1$ and an absolute electrical resistance evolution $AbsR_P(t)$ between the electrical resistance $R_p(t)$ to an electrical resistance $R_{P,i}$ when the hydrocarbon fluid 30 was just changed.

For example, the measurement circuit 50 calculates the absolute viscosity evolution Absη(t) by means of the following formula:

$$Abs\eta(t)=\eta(t)-\eta i \tag{7}$$

wherein $\eta_i$ is the viscosity of fresh hydrocarbon fluid 30 at the predetermined temperature $T_1$ and η(t) is the dynamic viscosity at the measurement time t of the current hydrocarbon fluid 30 at the predetermined temperature $T_1$.

For example, the measurement circuit 50 calculates the absolute electrical resistance evolution $AbsR_P(t)$ with the following formula:

$$AbsR_P(t)=R_P(t)-R_{P,i} \tag{8}$$

wherein $R_{P,i}$ is the electrical resistance $R_P$ of fresh hydrocarbon fluid 30 at the predetermined temperature $T_1$ and $R_P(t)$ is the electrical resistance $R_P$ at the measurement time t of the current hydrocarbon fluid 30 at the predetermined temperature $T_1$.

Additionally, the measurement circuit 50 can calculate an absolute evolution for the density ρ and/or the electrical constant ε in the same way as described for the absolute dynamic viscosity evolution Absη(t).

The measurement circuit 50 saves the absolute dynamic viscosity evolution Absη(t) and the absolute electrical resistance evolution $AbsR_P(t)$ with a time t dependency in the data storage 45.

In an eighth filtering step 335, the measurement circuit 50 calculates a relative dynamic viscosity evolution Relη(t) of dynamic viscosity η(t) at the defined time t to the dynamic viscosity $\eta_i$ when the hydrocarbon fluid 30 has just been changed.

For example, the measurement 50 circuit calculates the relative dynamic viscosity evolution Relη(t) of the viscosity η with the following formula:

$$Rel\eta(t)=\frac{\eta(t)-n_i}{n_i}\cdot 100\% \tag{9}$$

FIG. 7 shows a diagram of the dynamic viscosity η and the relative dynamic viscosity Relη(t) evolution over the oxidation O and time t at the predetermined temperature $T_1$ of the hydrocarbon fluid 30. The dynamic viscosity η is depicted with a continuous line, the relative dynamic viscosity evolution Relη(t) is depicted with a dashed line.

In an eighth filtering step 335, the measurement circuit 50 also calculates a relative electrical resistance evolution $RelR_P(t)$ of the electrical resistance $R_P(t)$ at the measurement time t to the resistance $R_{P,i}$.

For example, the measurement circuit calculates the relative resistance evolution $RelR_P(t)$ of resistance $R_P(t)$ with the following formula:

$$RelR_P(t)=100\frac{R_P(t)-R_{P,i}}{R_{P,i}}\cdot 100\% \tag{10}$$

Additionally, the measurement circuit 50 can calculate a relative evolution for the density ρ and/or the electrical constant ε in the same way as described for the absolute dynamic viscosity evolution Relη(t).

The measurement circuit 50 saves the relative dynamic viscosity evolution Relη(t) and the relative electrical resistance evolution $RelR_P(t)$ in the data storage 45 with the time t dependency.

After the filtering steps 300-335, the measuring circuit 50 analyses the viscosity η and the resistance $R_P$ over time and/or Oxidation O.

FIG. 8 shows a diagram of the density ρ and the relative density evolution Relρ over the oxidation O and time t at the predetermined temperature $T_1$.

The density ρ is depicted with a continuous line, the relative density evolution Relρ is depicted with a dashed line.

FIG. 9 shows a diagram of the dielectric constant ε and the relative dielectric constant evolution Relε over the oxidation O and time t at the predetermined temperature $T_1$.

The dielectric constant ε is depicted with a continuous line, the relative dielectric constant evolution Relε evolution is depicted with a dashed line.

FIG. 10 shows a diagram of the electrical resistance $R_p$ and the relative electrical resistance evolution $RelR_p(t)$ over the oxidation O and time t at the predetermined temperature $T_1$.

The electrical resistance $R_p$ is depicted with a continuous line, the relative electrical resistance evolution $RelR_p(t)$ is depicted with a dashed line.

In FIGS. 7 to 10, an increasing oxidation O relates to an increase of time t in which the hydrocarbon fluid 30 is used under oxidation conditions e.g. with a temperature T over a predetermined value. Instead of the oxidation O, the hydrocarbon fluid 30 shows nearly the same behaviour with nitration. Furthermore, the FIGS. 7 to 10 show a typical aging behaviour of engine oils. In the case the hydrocarbon fluid 30 is a hydraulic oil, the behaviour is slightly different.

In the present first embodiment, the hydrocarbon fluid 30 may reach its end of useful life in two different scenarios which limit the useful time of the hydrocarbon fluid 30.

In a first scenario, the hydrocarbon fluid 30 mainly oxidates and/or nitrates over time t. The other parameters of the hydrocarbon fluid 30 behave typically over time.

In a second scenario, the quality of the hydrocarbon fluid 30 mainly decreases because the alkaline reserve decreases. The end of useful lifetime of the hydrocarbon fluid 30 is reached in the second scenario when the hydrocarbon fluid 30 has only a short (predetermined)alkaline reserve.

In an eleventh step 250, the measurement circuit 50 analyses the absolute electrical resistance evolution $AbsR_P(t)$ and/or the relative electrical resistance evolution $RelR_P(t)$ over time t and/or oxidation O (compare FIG. 10, in FIG. 10 the absolute electrical resistance evolution $AbsR_P(t)$ is not shown). During monitoring the absolute electrical resistance evolution $AbsR_P(t)$ and/or the relative electrical resistance evolution $RelR_P(t)$ and/or the electrical resistance $R_P$ over time t and/or oxidation, the measurement circuit 50 can provide a first information signal regarding the quality of the hydrocarbon fluid in view of the evolution the determined multiple parameters of the sensor device 20 after every eleventh step 250.

The measurement circuit 50 determines the usage of the hydrocarbon fluid 30 in a first time period 500 after the beginning 505 of the use of the new hydrocarbon fluid 30 by detecting a first increase 510 of the relative and/or absolute electrical resistance evolution $AbsR_p$, $Rel_{Rp}$ over time t and/or oxidation O. Instead or additionally of the relative and/or absolute electrical resistance evolution $AbsR_p(t)$, $Rel_{Rp}(t)$ the measurement circuit 50 can also analyse the electrical resistance $R_P$ to determine the first time period 500.

The first increase 510 comprises a positive first gradient $dAbsR_p/dO$, $dRelR_p/dO$ and/or a positive second gradient $dAbsR_p/dt$, $dRelR_p/dt$ and/or a further gradient $dR_p/dO$, $dR_p/dt$. The first time period 500 is limited by the beginning 505 of the use of the fresh hydrocarbon fluid 30 and by a maximum value 165 of the electrical resistance $R_P$, respective relative and/or absolute electrical resistance evolution $AbsR_p(t)$, $Rel_{Rp}(t)$ over time t and oxidation O.

In the first time period 500, the value of the electrical resistance $R_p$ increases from a starting value 160 to the maximum value 165. In the maximum value 165, the first and second gradient $dAbsR_p/dO$, $dRelR_p/dO$, $dAbsR_p/dt$, $dRelR_p/dt$ of the relative and absolute electrical resistance evolution $AbsR_p$, $Rel_{Rp}$ over the oxidation O (and time t) and/or the further gradient $dR_p/dO$, $dR_p/dt$ are zero for the first time. Instead or additionally of the relative and/or absolute electrical resistance evolution $AbsR_p(t)$, $Rel_{Rp}(t)$ the measurement circuit 50 can also analyse the electrical resistance $R_P$ to determine the first decrease 516.

The measurement circuit 50 determines a second time period 515 of the quality of the hydrocarbon fluid 30 which follows after the first time period 500 by determining a decrease 516 of the absolute electrical resistance evolution $AbsR_P(t)$ and/or the relative electrical resistance evolution $RelR_P(t)$ and/or the electrical resistance $R_P$ over the oxidation O and time t (cf. FIG. 10). The decrease 516 in the second time period 515 can be detected by a negative first and/or second gradient $dAbsR_p/dO$, $dRelR_p/dO$, $dAbsR_p/dt$, $dRelR_p/dt$ and/or further gradient $dR_p/dO$, $dR_p/dt$.

In case the hydrocarbon fluid 30 is a hydraulic oil, the hydraulic oil does not comprise the first increase 510. Instead of the first increase 510 the hydraulic oil starts after the begin 505 of the hydraulic oil with the first decrease 516, which is detected by the measurement circuit 50.

During the first and the second time period 500, 505, the measurement circuit 50 can in short time intervals or quasi continuously provide the information about the quality of the hydrocarbon fluid 30 regarding the absolute difference Abs (TBN−TAN) between the total base number (TBN) and the total acid number (TAN) via the first information signal that the quality of the hydrocarbon fluid 30 is allowable and the end of useful lifetime has not been reached.

After the second time period 515, a third time period 520 of the quality of the hydrocarbon fluid 30 follows. The measurement circuit 50 determines a beginning of the third time period 520 by detecting a (global) minimum value 175 of the absolute electrical resistance evolution $AbsR_P(t)$ and/or relative electrical resistance evolution $RelR_P(t)$ and/or electrical resistance $R_P$ by determining that the first and/or the second gradient $dAbsR_p/dO$, $dRelR_p/dO$, $dAbsR_p/dt$, $dRelR_p/dt$ and/or the further gradient $dR_p/dO$, $dR_p/dt$ is/are zero for a second time (cf. FIG. 10). When the measurement circuit 50 determines a second increase 525 following the global minimum value 175, the measurement circuit 50 provides a second information signal or a third information signal.

The steps 230 to 250 are repeated until the measurement circuit 50 determines the second increase 525 of the absolute electrical resistance evolution $AbsR_P(t)$ and/or relative electrical resistance evolution $RelR_P(t)$ and/or the electrical resistance $R_P$.

Figure 11:
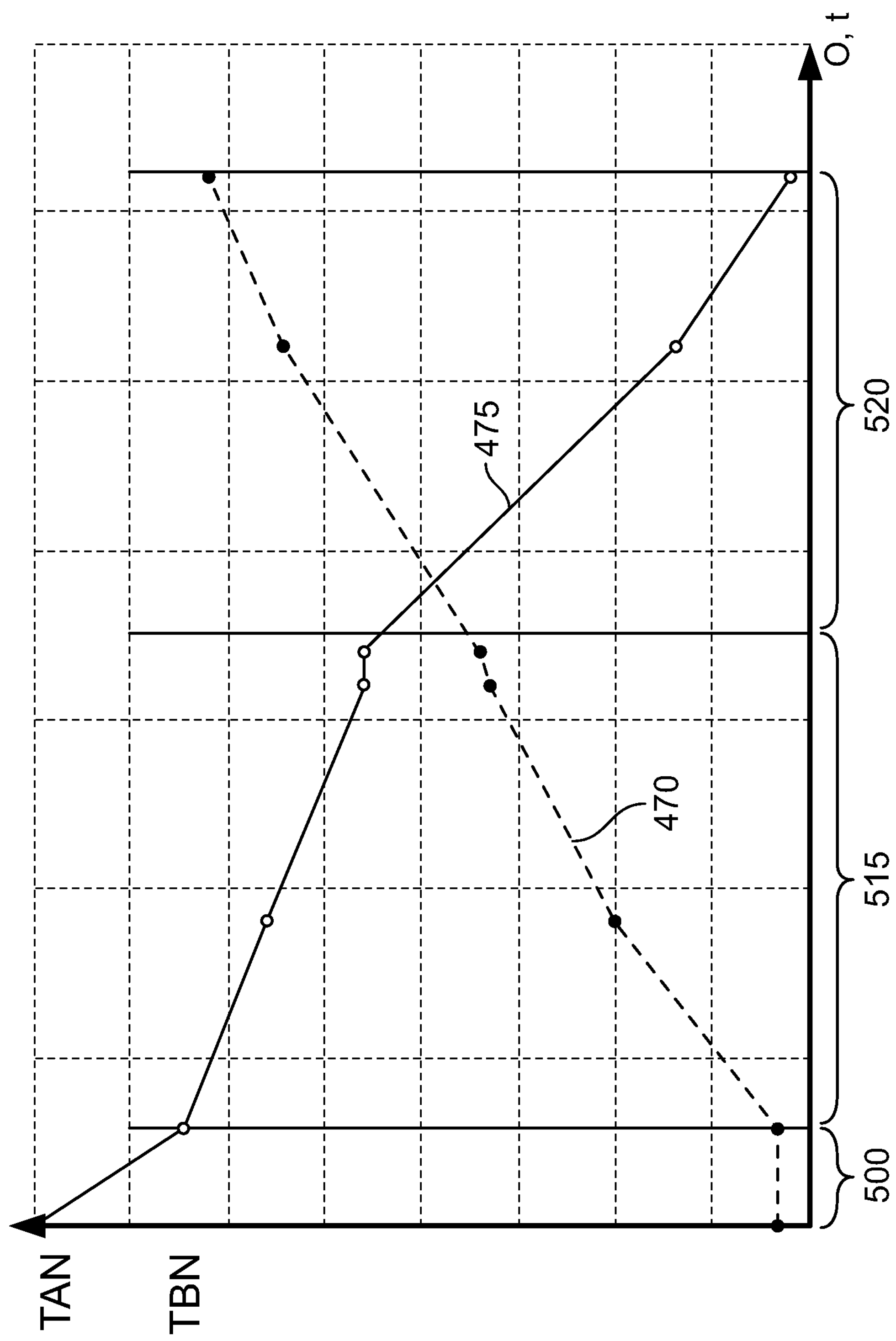
FIG. 11 shows a diagram of the total acid number (TAN) and the total base number (TBN) over time t and oxidation O.
Figure 12:
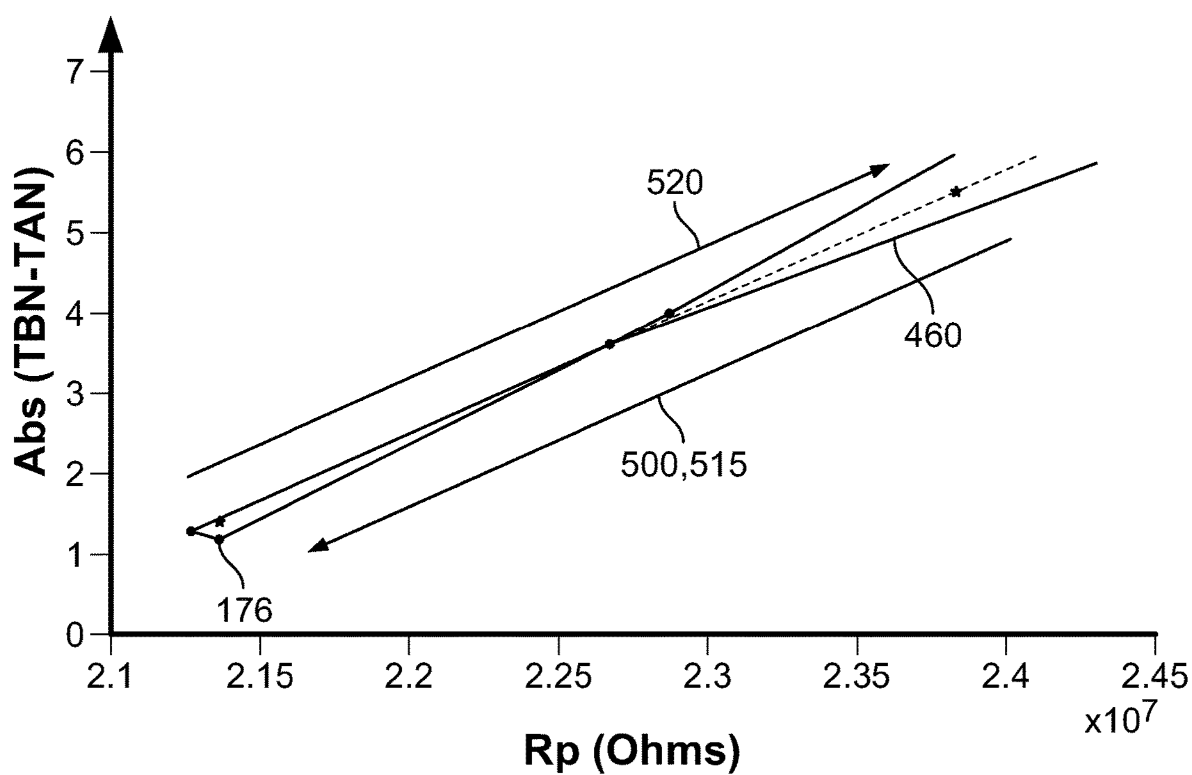
FIG. 12 shows a diagram of the absolute difference between the total base number (TBN) and the total acid number (TAN) over resistance $R_p$.
Figure 13:
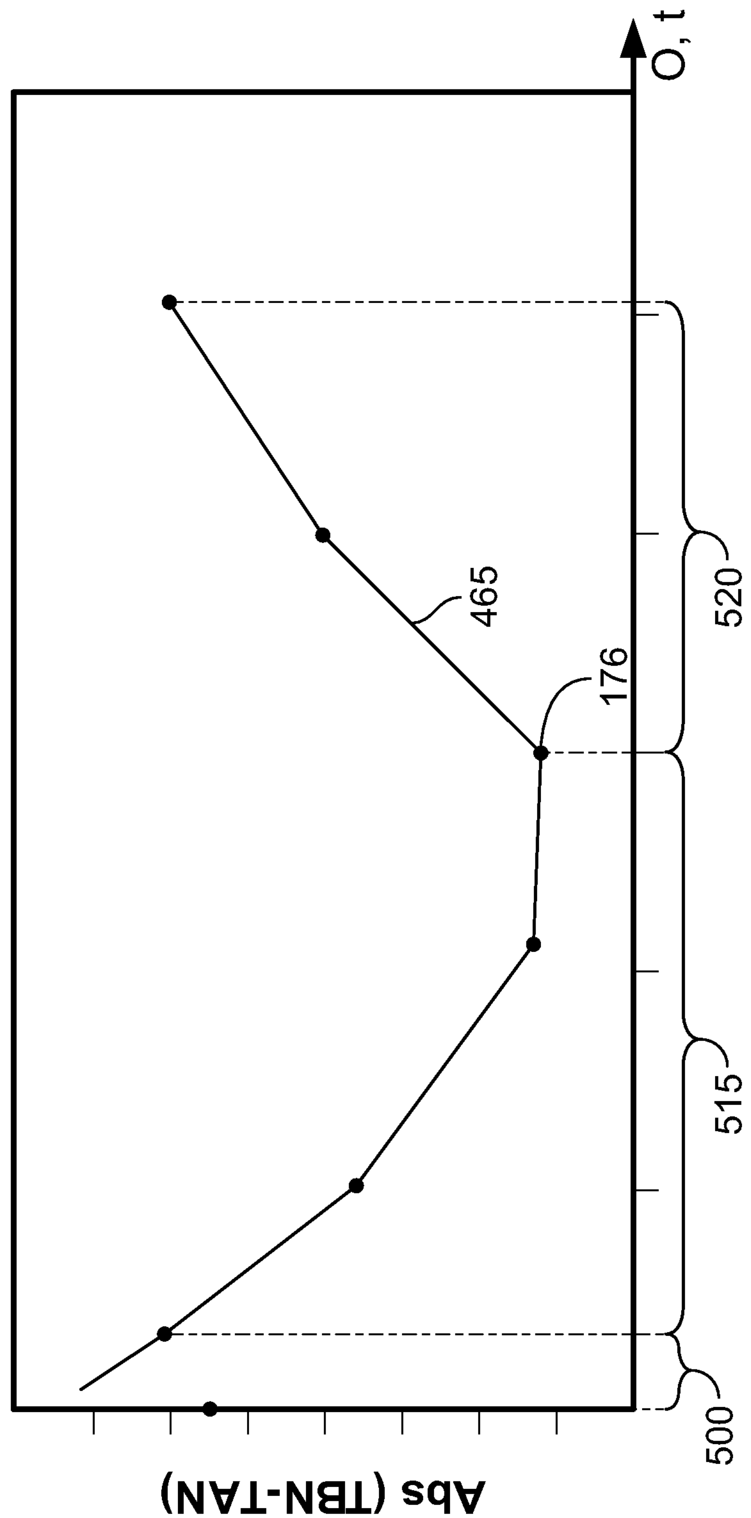
FIG. 13 depicts a diagram of the absolute difference between the total base number (TBN) and the total acid number (TAN) over oxidation O and time t.

FIG. 11 shows a diagram of the total acid number (TAN) and the total base number (TBN) over time and oxidation O. FIG. 12 shows a diagram of the absolute difference between the total base number (TBN) and the total acid number (TAN) over resistance $R_p$. FIG. 13 shows a diagram of the absolute difference between the total base number TBN and the total acid number TAN over oxidation O and time t.

In FIG. 11, a first second graph 470 shows the total acid number (TAN) and a second graph 475 shows the total base number (TBN) over the oxidation O and the time t. In FIG. 12, a third graph 460 shows the absolute difference Abs (TBN−TAN) of the total base number (TBN) and the total acid number (TAN) over the electrical resistance $R_P$. In FIG. 13, a fourth graph 465 shows the absolute difference Abs (TBN−TAN) of the total base number (TBN) and the total acid number (TAN) over the oxidation O and the time t.

Over the first time period 500 the values of the total acid number (TAN) are constant over oxidation O and time t. In the second time period 515 and the third time period 520, the values of the total acid number (TAN) increase (cf. FIG. 11).

Over the first time period 500, the values of the total base number (TBN) rapidly decrease over oxidation O and time t. In the second time period 515 and the third time period 520, the values of the total base number (TAN) decrease over oxidation O and time t in a more limited extend than in the first time period 500. At the end of the second time period 515, the first and the second graph 470, 475 cross each other or have nearly the same values (cf. FIG. 11).

In the first and second time period 500, 505, the absolute difference Abs(TBN−TAN) of the total base number (TBN) and the total acid number (TAN) decreases over the oxidation O and the time (compare FIG. 13). In FIG. 12, the decrease of the absolute difference Abs(TBN−TAN) of the total base number (TBN) and the total acid number (TAN) is marked with an arrow from top right to bottom left.

The absolute difference of the total base number (TBN) and the total acid number (TAN) reaches a minimum value 176 at the end of the second time period 500. Thus, the second information signal and the third information signal correspond to an information that the hydrocarbon fluid 30 has only a short reserve time which corresponds to the third time period 520 until all the alkaline reserve is finally used up and the hydrocarbon fluid 30 is at the end of its lifetime (at the end of the third time period 520). In FIG. 12, the increase of the absolute difference Abs(TBN−TAN) of the total base number (TBN) and the total acid number (TAN) is marked with an arrow from bottom left to top right.

In parallel or in series to the eleventh step 250 the measurement circuit 50 performs a twelfth step 255. In the twelfth step 255, the measurement circuit 50 determines a change of the absolute dynamic viscosity evolution Absη(t) and/or the relative viscosity evolution Relη(t) and/or the viscosity η over time t and/or oxidation O by determining a third gradient dAbsη/dt, dRelη/dt, dη/dt (compare FIG. 7).

In a thirteenth step 260, the measurement circuit 50 compares the determined third gradient dAbsη/dt, dRelη/dt, dη/dt with a predefined threshold S. If the third gradient dAbsη/dt, dRelη/dt, dη/dt is higher than the predefined threshold S, the measurement circuit 30 proceeds with a fourteenth step 265. If the third gradient dAbsη/dt, dRelη/dt, dη/dt is lower than the predefined threshold S, the measurement circuit 30 proceeds with a fifteenth step 270.

During the first time period 500 and the second time period 515, the measurement circuit 50 determines that the third gradient dAbsη/dt, dRelη/dt, dη/dt is smaller than the predefined threshold S.

In the fourteenth step 265 following the thirteenth step 260 at the beginning of the third time period 520, the measurement circuit 50 determines a third (predetermined) increase 530 of the third gradient dAbsη/dt, dRelη/dt, dη/dt that exceeds the predefined threshold S and determines the first scenario. The second information signal with the information on the quality relates to the first scenario of the hydrocarbon fluid 30.

In the first scenario, the end of useful lifetime of the hydrocarbon fluid 30 is reached because the hydrocarbon fluid 30 is oxidated and/or nitrated. The oxidation O and/or the nitration reduce the absolute difference of the total base number (TBN) and the total acid number (TAN). The second information signal is only provided when the second increase 525 of the absolute electrical resistance evolution $AbsR_P(t)$ and/or the relative electrical resistance evolution $RelR_P(t)$ and/or the electrical resistance $R_P$ and the third increase 530 of the change (dAbsη/dt, dRelη/dt, dη/dt) of viscosity η are detected in a third predetermined time period 535 and are preferably determined simultaneously. The third predetermined time period 535 is shorter than the first determined time period 500 and/or the second determined time period 515.

In the fifteenth step 270, the measurement circuit 50 detects that the third gradient $dAbs_\eta(t)/dt$, $dRelR_\eta(t)/dt$, dη/dt is lower than the threshold S and provides the third information signal with an information that correlates to the second scenario at which the hydrocarbon fluid 30 reaches its end of useful lifetime only because of the minimal difference of the total base number (TBN) and the total acid number (TAN) having the short reserve time since the alkaline reserve is nearly used up. The oxidation O and/or the nitration of the hydrocarbon fluid 30 in the second scenario is reduced compared to the first scenario.

In a sixteenth step 275, the information about the quality of the hydrocarbon fluid 30 transmitted with the second information signal or the third information signal is stored in the data storage 45 or an error memory. The information can be taken into account for an error analysis of the machine to detect e.g., why the hydrocarbon fluid 30 reaches its end of useful lifetime. For the error analysis the actual value of the total acid number (TAN) and/or total base number (TBN) can be additionally taken into account, as well.

In the sixteenth step 275, the second information signal or the third information signal is provided at the interface 40 for the signalling device 35. The signalling device 35 detects the second information signal or the third information signal and changes its status from deactivated to activated in order to signalize the end of useful lifetime of the hydrocarbon fluid 30 and that a change of the hydrocarbon fluid 30 has to be performed.

To precisely detect further errors of the machine, the measurement circuit 50 can also take into account the change of the dielectric constant ε (compare FIG. 9) and/or the density ρ (compare FIG. 8) of the hydrocarbon fluid 30 over time t and oxidation O.

After providing the second information signal or the third information signal with the information on the hydrocarbon fluid quality, the repeating of the determining steps (seventh and eight step 230, 235) of the resistance $R_p$ and/or viscosity η is stopped.

Alternatively, after providing the second information signal or the third information signal with the information, the steps 205 to 275 are performed only for a fourth predetermined time period, wherein the fourth predetermined time period is shorter than a backup time, e.g., the reserve time of the alkaline reserve, in which the hydrocarbon fluid 30 can still be used before the hydrocarbon fluid 30 is completely degraded.

Additionally, in a seventeenth step 280, the measurement circuit 50 can determine a level of contamination or ageing of the hydrocarbon fluid 30 on the basis of a risk management parameter to detect a dramatic change in the composition of the hydrocarbon fluid 30 for the application.

The risk management parameter can be a further predefined threshold, for example a predetermined fifth time period or a predetermined event, for example a restart of the system 10 and/or an engine.

By means of the seventeenth step 280, it is guaranteed that a contamination of the hydrocarbon fluid 30 for example with water, coolant, fuel contaminations, a wrong fluid voluntary or involuntary filling into the hydrocarbon fluid 30 can be detected.

These contaminations are associated with high evolution speed. For example, water contamination could happen between two working engine phases and induces an increase of dielectric constant ε measurement after an engine is switched on in comparison to the dielectric constant ε before the engine is last switched off.

For example, if the measurement circuit 50 detects the following relative evolutions at a second temperature $T_2$=50° C.:

$$Rel\eta=0\%,\ Rel\rho=0\%,\ Rel\varepsilon>9\% \text{ and } RelR_p<-3\%$$

the hydrocarbon fluid 30 has a high probability of being contaminated with more than 5000 ppm water (or more than 10000 ppm coolant).

Figure 14:
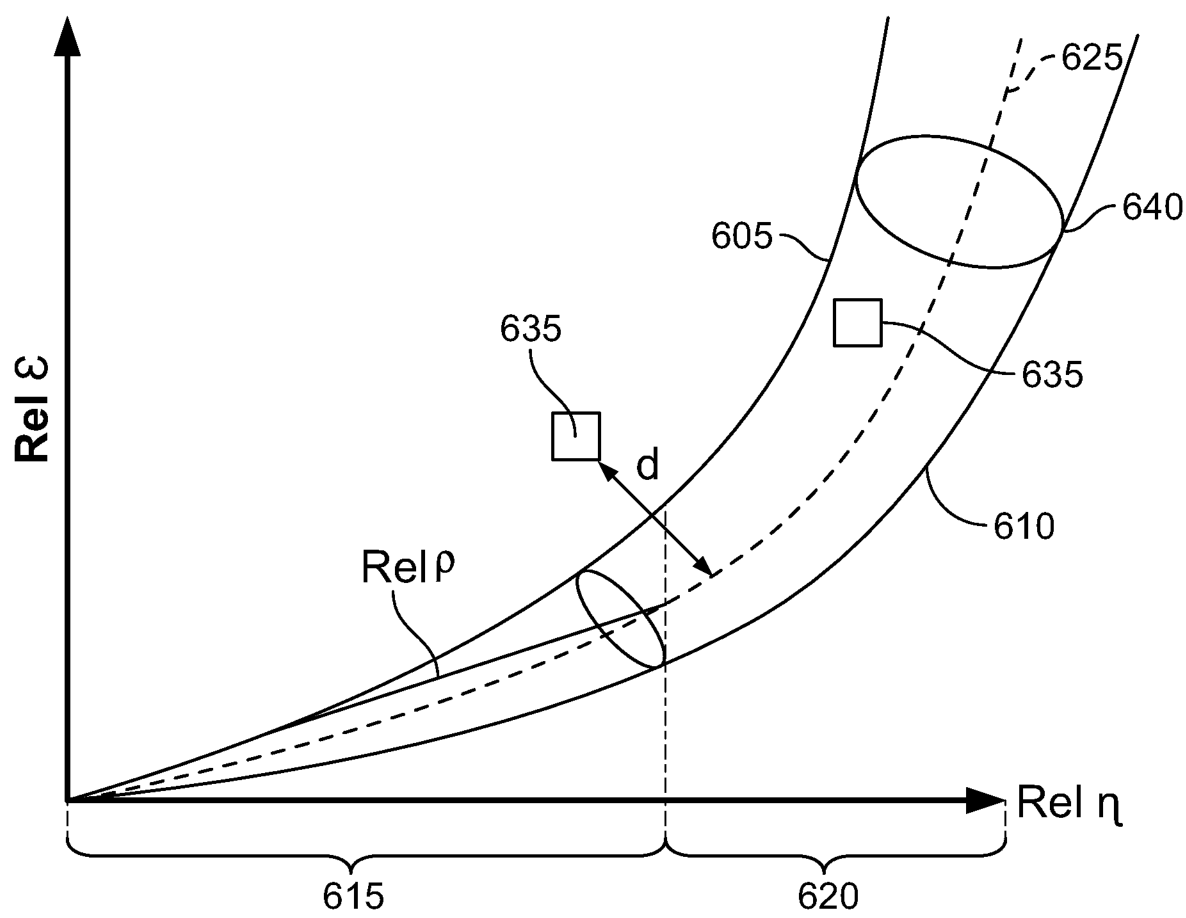
FIG. 14 depicts a 3D-diagram of the dynamic viscosity $\eta$, density $\delta$ and dielectric constant $\varepsilon$ and a tolerance band.

FIG. 14 shows an exemplary 3D-diagram of the dynamic viscosity η, density δ and dielectric constant ε and a tolerance band 600 with an upper limit 605 and a lower limit 610. Due to the 3D-diagram, the tolerance band 600 comprises a tube form.

In FIG. 14 the dotted line 625 represents the average oxidation trend for one specific application of the hydrocarbon fluid 30. In order to consider the possible variabilities between different ageing processes even in similar application conditions, the typical oxidation trend 630 is preferably represented by the tolerance band 600. The tolerance band 600 comprises an upper limit 605 and a lower limit 610.

The oxidation O of the hydrocarbon fluid 30 is a particular ageing process that necessarily happens during all hydrocarbon fluid lifetime. Additionally, in an eighteenth step 285 the measurement circuit 50 can calculate and store an oxidation trend 635 on the basis of the relative and/or absolute electrical resistance evolution $AbsR_p(t)$, $RelR_p(t)$ and/or previously determined relative and/or absolute dynamic viscosity evolution Absη(t), Relη(t), relative and/or absolute density evolution Absρ(t), Relδ(t), and/or relative and/or absolute dielectric constant evolution Absε(t), Relε(t) and can calculate a relative distance d to said average oxidation trend 625 in a future time period 620 on the basis of an at least the relative and/or absolute electrical resistance evolution $AbsR_p(t)$ and/or a previously determined relative and/or absolute dynamic viscosity evolution Absη(t), Relη (t), a relative and/or absolute density evolution Absρ(t), Relδ(t), and/or a relative and/or absolute dielectric constant evolution Absε(t), Relε(t) over a past time period 615 and a predetermined trend parameter.

Two cases are considered for measurement in FIG. 14.

In Case 1 the oxidation trend 635 is inside of the tolerance band 600, which means that hydrocarbon fluid 30 follows an expected oxidation process, whereas in Case 2 the oxidation trend 635 is out of the tolerance band 600, which means that hydrocarbon fluid 30 is abnormally contaminated.

In a nineteenth step 290, the measurement circuit 50 compares the relative distance d with the tolerance band 600 and provides a third signal at the interface when the relative distance d is higher than the tolerance band 600. The third signal is detected by the signalling device 35 to signal that the hydrocarbon fluid 30 ages out of the typical behaviour.

The calculation of the distance d of the hydrocarbon fluid 30 to the tolerance band 600 allows a detection and a precise forecast of the contaminations of the hydrocarbon fluid 30.

In a twentieth step 295, the measurement circuit 50 detects the contamination of the hydrocarbon fluid 30 by comparing the oxidation trend 635 with a further predefined threshold 640. The further predefined threshold 640 limits the tolerance band 600 between the upper limit 605 and the lower limit 610 in a future time period 620. The fourth signal is detected by the signalling device 35 which signals on the basis of the fourth signal the lifetime of the hydrocarbon fluid 30.

If the oxidation trend 635 exceeds the predefined further threshold 640, the measurement circuit 50 can calculate a possible lifetime of the hydrocarbon fluid 30 on the basis of the further threshold 640 and the oxidation trend 635 and provides a corresponding fourth signal at the interface 40. Also, different further thresholds 640 can be provided for different possible long term contaminations of the hydrocarbon fluid 30.

After a predetermined event which can for example be a restart of the system 10 or a predetermined sixth time period, for example every operating hour, the steps 225 to 295 are repeated and an actual state of the hydrocarbon fluid 30 is again monitored and analysed.

Figure 15:
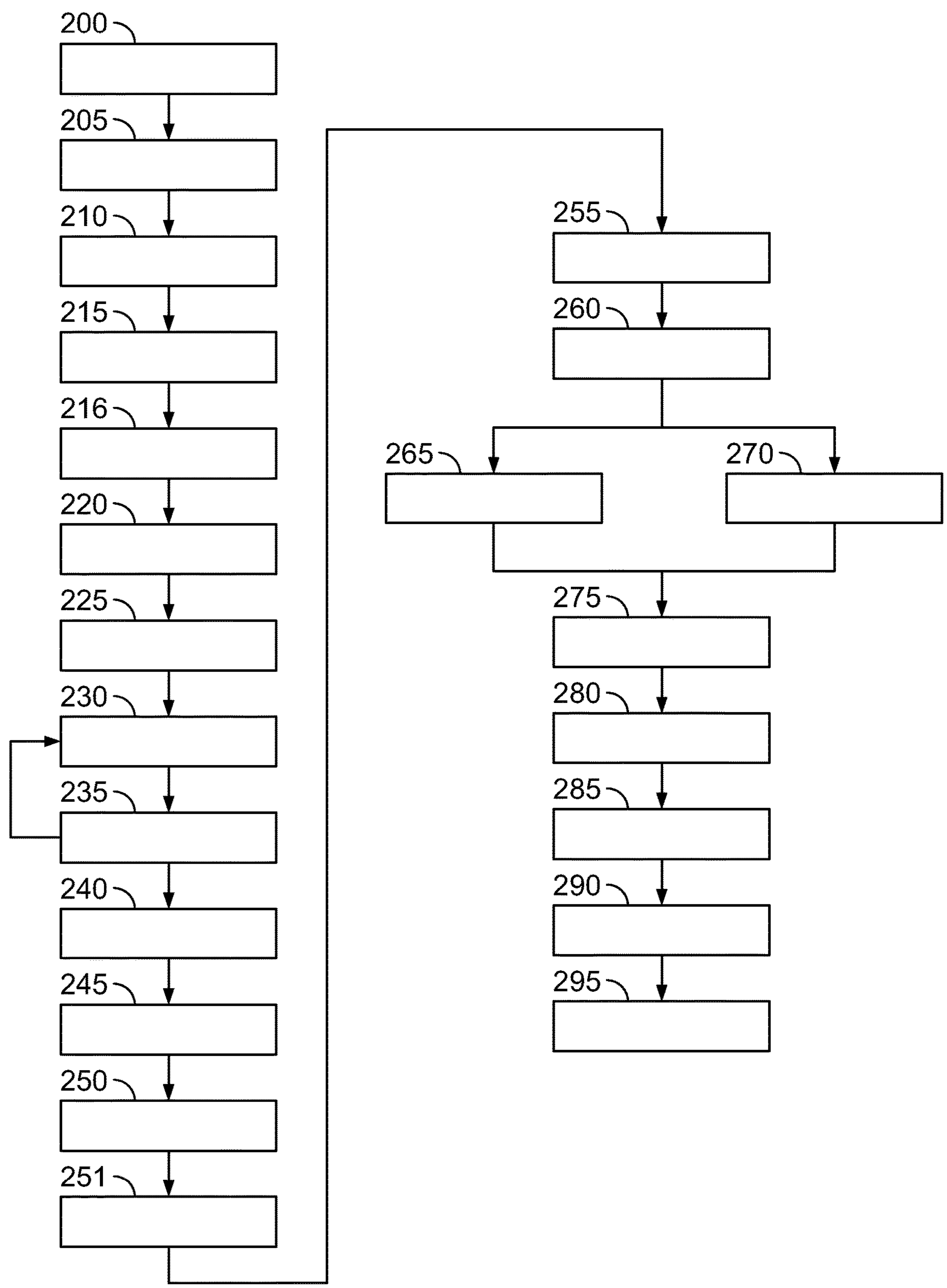
FIG. 15 depicts a flow chart of a method according a second embodiment to determine the quality of a hydrocarbon fluid of the system.

FIG. 15 shows a flow chart of a method according to a second embodiment for determining the quality of a hydrocarbon fluid of the system.

The method is basically identical to the method described in FIG. 4. In the following, only the differences between the method according to the second embodiment and the method according to the first embodiment are described. In the second embodiment, the composition of the hydrocarbon fluid 30 is known.

In a first additional step 216 following the forth step 215, start values of the total base number (TBN) and the total acid number (TAN) are determined for a specific type of a fresh hydrocarbon fluid 30, for example by a lab analysis. The start value of the total acid number (TAN) for example can be determined by the standard test method ASTM D664 and the start value for the total acid number (TAN) can be determined by the standard test method ASTM D2896. Also, a start difference between the values of the total base number (TBN) and the total acid number (TAN) can be calculated on the basis of the determined start values of the total acid number (TAN) and the of the total base number (TBN). The fifth step 220 is executed after the first additional step 216. The start values can be stored in the data storage 45. The start values can also be provided by a manufacturer of the hydrocarbon fluid 30.

In addition to the steps 215 to 250, the measurement circuit 50 can calculate the start values of the total acid number (TAN) and the total base number (TBN) and the determined absolute resistance $AbsR_P(t)$ and/or relative resistance $RelR_P(t)$ actual values of the actual total acid number TAN and the total base number TBN and/or an actual value of the absolute difference Abs(TBN−TAN) between the total base number (TBN) and the total acid number (TAN) in a second additional step 251 following the eleventh step 250 on the basis of a further predetermined parameter.

The further predetermined parameters can be a characteristic diagram of the behaviour of the total acid number (TAN) and the total base number (TBN) over absolute resistance $AbsR_P(t)$ and/or relative resistance $RelR_P(t)$ and/or a characteristic diagram of the behaviour of the absolute difference Abs(TBN−TAN) of the total base number (TBN) and the total acid number (TAN) over the absolute resistance $AbsR_P(t)$ and/or the relative resistance $RelR_P(t)$.

The actual values of the total acid number (TAN) and/or the total base number (TBN) an/or the absolute difference Abs(TBN−TAN) between the total base number (TBN) and the total acid number (TAN) can be stored in the data storage 45. The actual values of the total acid number (TAN) and the total base number (TBN) and/or the actual value of the absolute difference Abs(TBN−TAN) between the total base number (TBN) and the total acid number (TAN) can be provided as an information with the first information signal. With the additional second step 251, the alkaline reserve can be determined without a lab analysis in an easy manner.

In addition, in case the used hydrocarbon fluid 30 is known a predetermined end value of the absolute value of the difference of the total acid number (TAN) and the total base number (TBN) of the hydrocarbon fluid (30) corresponding to an end of the life of the hydrocarbon fluid (30) can be determined for example with a lab analysis. The end value can be stored in the data storage 45. Additionally, or alternatively, a predetermined end value of electrical resistivity $R_B$ of the hydrocarbon fluid 30 corresponding to an end of the life of the hydrocarbon fluid 30 can be determined in a lab analysis and be saved in the data storage 45. On the basis of a further predetermined parameter, the predetermined start value of the electrical resistance $R_{P,\ i2}$ for example the maximum value of $R_P$, the predetermined end value of electrical resistivity $R_{P,\ E}$, for example the minimum value 175, and the determined actual electrical resistivity $R_P$ a remaining lifetime (RUL) of the hydrocarbon fluid regarding the absolute value of the difference of the total acid number (TAN) and the total base number (TBN) is determined.

The remaining useful life (RUL) of the hydrocarbon fluid 30 regarding the resistance Rp can be defined as:

$$RUL(Rp)=100*(R_{P,E}-Rp)/(R_{P,E}-R_{P,i2})$$

Additionally, or alternatively, a predetermined end value of dynamic viscosity $\eta_E$ of the hydrocarbon fluid 30 corresponding to an end of the life of the hydrocarbon fluid 30 regarding the viscosity can also be determined in the lab analysis and be saved in the data storage 45. On the basis of the further predetermined parameter, a start value of the dynamic viscosity $\eta_0$ at the begin of the use of the hydrocarbon fluid or at the time t or the oxidation O of the hydrocarbon fluid reached the maximum value of $R_P$, and the predetermined end value of dynamic viscosity $\eta_E$ and the determined actual dynamic viscosity $\eta$ a remaining lifetime (RUL) of the hydrocarbon fluid regarding the dynamic viscosity $\eta$ is determined.

The remaining useful life (RUL) of the hydrocarbon fluid 30 regarding to the dynamic viscosity $\eta$ can be defined as:

$$RUL(\eta)=100*(\eta_E-\eta)/(\eta_E-\eta_0)$$

The remaining useful life (RUL) of the hydrocarbon fluid 30 regarding the resistance Rp and/or the remaining useful life (RUL) of the hydrocarbon fluid 30 regarding to the dynamic viscosity $\eta$ provide a good information about the current state regarding the oxidation and/or the nitration of the hydrocarbon fluid 30.

Furthermore, an information on the remaining lifetime (RUL) of the hydrocarbon fluid with the information signal can be provided.

The (global) minimum value 175 is in this case predetermined, and can for example be determined by previous executed test for the hydrocarbon fluid 30 or a lab analysis. The first information signal can contain an information about the remaining useful life (RUL).

The second embodiment of the method has the advantage that a precise information regarding the remaining useful life and the total acid number (TAN) and the total base number (TBN) can be provided in addition to the other physical parameters such as density and viscosity.

It should be pointed out that the order of the above described steps 200-295, 300-335 is the preferred order. Of course, the order can be different. Furthermore at least one step 200-295, 300-335 may be omitted and/or the order of the steps can be different.

The described system can also be adopted to nearly identical systems and said methods should be considered as possible solutions. Each of the steps 200-275, 300-340 has specific characteristics that can be induced by specific adjustments.

Also, the determined relative and/or absolute electrical resistance evolution $AbsR_p(t)$, $RelR_P(t)$, and/or previously determined relative and/or absolute dynamic evolution viscosity $Abs\eta(t)$, $Rel\eta(t)$, relative and/or absolute density $Abs\rho(t)$, $Rel\rho(t)$ and/or relative and/or absolute dielectric constant evolution $Abs\varepsilon(t)$, $Rel\varepsilon(t)$ can be additionally used to distinguish the oxidation O of the hydrocarbon fluid 30 from other contamination of the hydrocarbon fluid 30 such as soot contamination, fuel dilution, water/coolant dilution, metal contamination, wrong fluid detection.

With the improved method and the improved analysis system 10, the accuracy in detecting the quality of the hydrocarbon fluid 30, particularly of additive conductive hydrocarbon fluids, can be improved. Nor is any additional sensor equipment needed so that the analysis system 10 can be easily mounted at the means 25 for containing the hydrocarbon fluid 30.

Also, a precise prediction of remaining useful life of the hydrocarbon fluid and inducing hydrocarbon fluid change interval optimization, minimization of dramatic engine failure and maintenance costs reduction is provided.

Also, the analysis system 10 and the method could easily be integrated in already existent systems. The new system 10 and the new method are also directly usable in combination with other systems, for example with a control unit of the vehicle or the combustion engine.

LIST OF REFERENCE NUMBERS

10 system
15 control unit
20 sensor device
25 means for containing a fluid composition
30 oil
35 signalling device
40 interface
45 data storage
50 measurement circuit
55 signal generator
60 receiver
65 first connection
70 second connection
75 third connection
76 further connection
77 error storage
80 compartment
85 mechanical resonator
90 sensor
100 fourth connection
105 fifth connection
115 tine
120 quartz crystal centre section
125 electrode
130 shell surface
135 first electrode section
140 second electrode section
145 electric field
149 second measurement response signal
150 first calibrating response signal
151 second calibrating response signal
155 first measurement response signal
156 first distribution
157 first sweep
158 second distribution
159 second sweep
160 starting value
161 third distribution
162 third sweep
165 maximum value
175 minimum value of the of the absolute electrical resistance

176 minimum value of the absolute difference
200 first step
205 second step
210 third step
215 fourth step
220 fifth step
225 sixth step
230 seventh step
235 eighth step
240 ninth step
245 tenth step
250 eleventh step
255 twelfth step
260 thirteenth step
265 fourteenth step
270 fifteenth step
275 sixteenth step
280 seventeenth step
285 eighteenth step
290 nineteenth step
295 twentieth step
300 first filtering step
305 second filtering step
310 third filtering step
315 fourth filtering step
320 fifth filtering step
325 sixth filtering step
330 seventh filtering step
335 eight filtering step
400 electric model
405 first electrical path
410 second electrical path
415 third electrical path
420 fourth electrical path
425 resistance ($R_p$)
430 first impedance (CpSens)
435 second impedance ($C_p$)
440 further resistance ($R_0$)
445 third impedance ($C_s$)
450 inductance ($L_0$)
455 additional term
460 third graph
465 fourth graph
470 first graph
475 second graph
500 first time period
505 begin of the use of the new fluid composition
510 first increase
515 second time period
516 decrease
520 third time period
525 second increase
530 predetermined increase of the change of viscosity
535 third predetermined time period
600 tolerance band
605 upper limit
610 lower limit
615 past time period
620 future time period
625 average oxidation trend
630 typical oxidation trend
635 oxidation trend
640 further threshold

What is claimed is:

1. A method for determining a quality of a hydrocarbon fluid, comprising the following steps:

determining an electrical resistivity ($R_p$) of the hydrocarbon fluid by means of a sensor device;

repeating the determining step for the electrical resistivity ($R_P$) over time (t);

monitoring the resistivity ($R_P$) of the hydrocarbon fluid over time;

determining a use of the hydrocarbon fluid under predetermined conditions;

determining a change of resistivity ($dR_p/dt$, $dR_P/dO$) over time (t), where "O" is oxidation;

monitoring the change of resistivity ($dR_p/dt$, $dR_P/dO$) of the hydrocarbon fluid over time (t); and providing a quality information about an absolute value of a difference of a total base number (TBN) and a total acid number (TAN) on the basis of the monitored change of resistivity ($R_P$).

2. The method according to claim 1 further comprising the steps of:

determining a predetermined decrease of the electrical resistivity ($R_P$) over time (t); and determining a predetermined increase of the electrical resistivity ($R_P$) over time (t) following the decrease of the electrical resistivity ($R_P$) over time (t);

wherein, when determining the increase of the electrical resistivity ($R_P$) following the decrease, an information about an end of a useful lifetime of the hydrocarbon fluid regarding the absolute value of the difference of the total base number (TBN) and the total acid number (TAN) is provided.

3. The method according to claim 2 further comprising the steps of:

determining a first time period by detecting a further predetermined increase of the electrical resistivity ($R_P$) over time (t);

determining a second time period following the first time period by detecting the predetermined decrease of the electrical resistivity ($R_P$) over time (t); and determining a beginning of a third time period following the second time period by detecting the predetermined increase of the electrical resistivity ($R_P$) over time (t).

4. The method according to claim 2 further comprising the steps of:

determining a dynamic viscosity ($\eta$) of the hydrocarbon fluid by means of the sensor device;

repeating the determining step for the viscosity ($\eta$) over time (t);

determining a change of viscosity ($\eta$) of the hydrocarbon fluid over time (t); and determining a predetermined increase of the change of viscosity ($\eta$);

wherein the increase of the change of viscosity ($\eta$) in combination with the increase of electrical resistivity ($R_P(t)$) provides an information on the quality of the hydrocarbon fluid regarding oxidation (O) and/or nitration of the hydrocarbon fluid and the difference of the total base number (TBN) and the total acid number (TAN).

5. The method according to claim 3 further comprising the steps of:

determining a dynamic viscosity ($\eta$) of the hydrocarbon fluid by means of the sensor device;

repeating the determining step for the viscosity ($\eta$) over time (t);

determining a change of viscosity ($\eta$) of the hydrocarbon fluid over time (t); and determining a predetermined increase of the change of viscosity ($\eta$);

wherein the increase of the change of viscosity (η) in combination with the increase of electrical resistivity ($R_P$(t)) provides an information on the quality of the hydrocarbon fluid regarding oxidation (O) and/or nitration of the hydrocarbon fluid and the difference of the total base number (TBN) and the total acid number (TAN).

6. The method according to claim 4:

wherein the change (dAbsη/dt, dRelη/dt) of the viscosity (η) is compared with a predetermined threshold (S);

wherein the information on the quality of the hydrocarbon fluid correlates to the oxidation (O) and/or the nitration of the hydrocarbon fluid and the difference of the total base number (TBN) and the total acid number (TAN) when the change (dAbsη/dt, dRelη/dt) of viscosity (η) exceeds the predetermined threshold (S); and wherein the information on the quality of the hydrocarbon fluid correlates to the difference of the total base number (TBN) and the total acid number (TAN) of the hydrocarbon fluid when the change (dAbsη/dt, dRelη/dt) of viscosity (η) is below the predetermined threshold (S).

7. The method according to claim 5:

wherein the change (dAbsη/dt, dRelη/dt) of the viscosity (η) is compared with a predetermined threshold (S);

wherein the information on the quality of the hydrocarbon fluid correlates to the oxidation (O) and/or the nitration of the hydrocarbon fluid and the difference of the total base number (TBN) and the total acid number (TAN) when the change (dAbsη/dt, dRelη/dt) of viscosity (η) exceeds the predetermined threshold (S); and wherein the information on the quality of the hydrocarbon fluid correlates to the difference of the total base number (TBN) and the total acid number (TAN) of the hydrocarbon fluid when the change (dAbsη/dt, dRelη/dt) of viscosity (η) is below the predetermined threshold (S).

8. The method according to claim 4:

wherein the information on the quality of the hydrocarbon fluid regarding oxidation (O) an/or nitration of the hydrocarbon fluid and the difference of the total base number (TBN) and the total acid number (TAN) is provided when the predetermined increase in the change (dAbsη/dt, dRelη/dt) of viscosity (η) exceeding the predetermined threshold (S), are detected in a first predetermined time period, preferably are determined simultaneously; and wherein the first predetermined time period is shorter than the first determined time period and/or the second determined time period.

9. The method according to claim 5:

wherein the information on the quality of the hydrocarbon fluid regarding oxidation (O) an/or nitration of the hydrocarbon fluid and the difference of the total base number (TBN) and the total acid number (TAN) is provided when the predetermined increase in the change (dAbsη/dt, dRelη/dt) of viscosity (η) exceeding the predetermined threshold (S), are detected in a first predetermined time period, preferably are determined simultaneously; and wherein the first predetermined time period is shorter than the first determined time period and/or the second determined time period.

10. The method according to claim 1:

wherein depending on the information an information signal is provided to signalize that the hydrocarbon fluid is about to reach its end of useful life and a change of the hydrocarbon fluid has to be carried out.

11. The method according to claim 2:

wherein after determining the increase of the electrical resistivity ($R_P$) in the determining step of the electrical resistivity ($R_p$) is stopped; or wherein after providing the information, the electrical resistivity ($R_p$) is only determined for a second predetermined time period; and wherein the second predetermined time period is shorter than a backup time in which the hydrocarbon fluid still can be used before the hydrocarbon fluid is completely degraded.

12. The method according to claim 1:

wherein the information is stored in a memory, preferably in an error register; and wherein the information is taken into account for an error analysis for a mechanical machine or a system, which uses the hydrocarbon fluid.

13. The method according to claim 1 further comprising the steps of:

applying a variable frequency input signal to a measurement circuit coupled with the sensor device;

varying the frequency (f) of the frequency input signal over a predetermined frequency range to obtain a frequency dependent response signal of the sensor device;

determining the electrical resistivity ($R_p$) of the hydrocarbon fluid on the basis of the response signal; and repeating the applying, varying and determining steps over time.

14. The method according to claim 13 comprising:

determining the viscosity (η) of the hydrocarbon fluid on basis of the response signal;

wherein the viscosity (η) and the electrical resistivity (Rp) are determined on basis of the same response signal.

15. The method according to claim 1:

wherein an information on a start value of the total acid number (TAN) and/or a start value of the total base number (TBN) of the hydrocarbon fluid at the beginning of the use of the hydrocarbon fluid is provided;

wherein on the basis of a predetermined parameter the resistivity ($R_P$) and the start value of the total acid number (TAN) and/or start value of the total base number (TBN) an actual value of the of the difference of the total acid number (TAN) and the total base number (TBN) is determined; and wherein the actual absolute value of the difference of the total acid number (TAN) and the total base number (TBN) is provided.

16. The method according to claim 15 further comprising:

providing a predetermined end value of the absolute value of the difference of the total acid number (TAN) and the total base number (TBN) of the hydrocarbon fluid corresponding to an end of the life of the hydrocarbon fluid; and/or providing a predetermined end value of electrical resistivity ($R_B$) of the hydrocarbon fluid corresponding to an end of the life of the hydrocarbon fluid;

wherein on the basis of a further predetermined parameter, the predetermined start value, the predetermined end value of electrical resistivity ($R_B$) and the determined actual electrical resistivity ($R_P$) a remaining lifetime of the hydrocarbon fluid regarding the absolute value of the difference of the total acid number (TAN) and the total base number (TBN) are determined; and wherein an information on the remaining lifetime of the hydrocarbon fluid is provided.

17. An analysing system that is designed to perform the method according to claim 1.

* * * * *